(12) United States Patent
Bertolero et al.

(10) Patent No.: US 7,226,448 B2
(45) Date of Patent: Jun. 5, 2007

(54) CARDIAC TREATMENT DEVICES AND METHODS

(75) Inventors: Arthur A. Bertolero, Danville, CA (US); Tamer Ibrahim, Oakland, CA (US); Daniel J. Conley, Santa Rosa, CA (US)

(73) Assignee: ESTECH, Inc. (Endoscopic Technologies, Inc.), Danville, CA (US)

( * ) Notice: Subject to any disclaimer, the term of this patent is extended or adjusted under 35 U.S.C. 154(b) by 296 days.

(21) Appl. No.: 10/410,618

(22) Filed: Apr. 8, 2003
(Under 37 CFR 1.47)

(65) Prior Publication Data
US 2004/0102771 A1    May 27, 2004

Related U.S. Application Data

(63) Continuation-in-part of application No. 10/272,446, filed on Oct. 15, 2002, now Pat. No. 6,849,075.

(60) Provisional application No. 60/337,070, filed on Dec. 4, 2001.

(51) Int. Cl.
*A61B 18/18* (2006.01)
(52) U.S. Cl. .................. 606/41; 607/130; 128/898
(58) Field of Classification Search ............ 606/41–50; 607/101, 102, 116, 122; 128/898; 600/374; 604/104–108, 115–116
See application file for complete search history.

(56) References Cited

U.S. PATENT DOCUMENTS

| | | | | |
|---|---|---|---|---|
| 5,423,805 A | * | 6/1995 | Brucker et al. | 606/15 |
| 5,593,405 A | * | 1/1997 | Osypka | 606/15 |
| 6,039,733 A | * | 3/2000 | Buysse et al. | 606/40 |
| 6,110,106 A | * | 8/2000 | MacKinnon et al. | 600/181 |
| 6,251,065 B1 | | 6/2001 | Kochamba et al. | |
| 6,511,416 B1 | | 1/2003 | Green, II et al. | |
| 6,514,250 B1 | | 2/2003 | Jahns et al. | |
| 6,522,905 B2 | | 2/2003 | Desai | |
| 6,527,767 B2 | | 3/2003 | Wang et al. | |
| 6,544,263 B2 | | 4/2003 | Morgan et al. | |
| 6,595,989 B1 | * | 7/2003 | Schaer | 606/41 |
| 2002/0177846 A1 | * | 11/2002 | Mulier et al. | 606/27 |

* cited by examiner

*Primary Examiner*—Roy D. Gibson
(74) *Attorney, Agent, or Firm*—Townsend and Townsend and Crew LLP

(57) ABSTRACT

Devices and methods provide for ablation of cardiac tissue for treating cardiac arrhythmias such as atrial fibrillation. Although the devices and methods are often be used to ablate epicardial tissue in the vicinity of at least one pulmonary vein, various embodiments may be used to ablate other cardiac tissues in other locations on a heart. Devices generally include at least one tissue contacting member for contacting epicardial tissue and securing the ablation device to the epicardial tissue, and at least one ablation member for ablating the tissue. Various embodiments include features, such as suction apertures, which enable the device to attach to the epicardial surface with sufficient strength to allow the tissue to be stabilized via the device. For example, some embodiments may be used to stabilize a beating heart to enable a beating heart ablation procedure. Many of the devices may be introduced into a patient via minimally invasive introducer devices and the like. Although devices and methods of the invention may be used to ablate epicardial tissue to treat atrial fibrillation, they may also be used in veterinary or research contexts, to treat various heart conditions other than atrial fibrillation and/or to ablate cardiac tissue other than the epicardium.

101 Claims, 12 Drawing Sheets

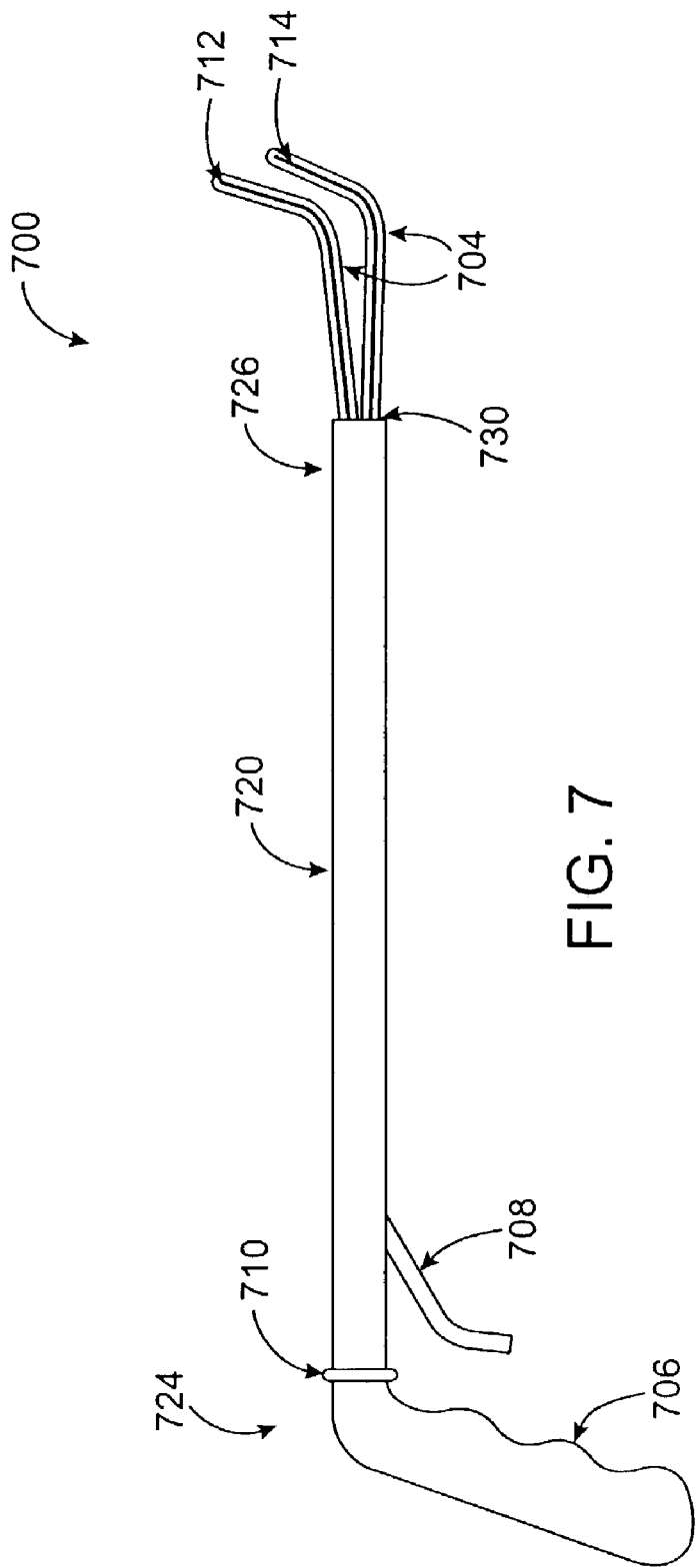
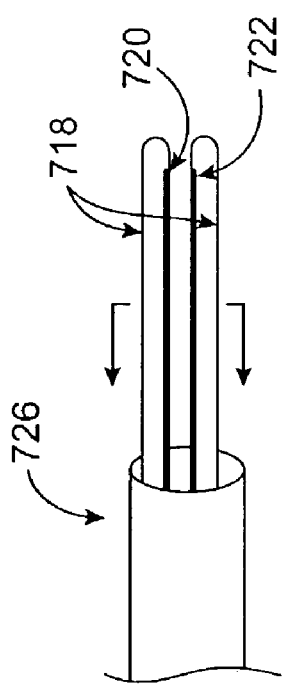
FIG. 7
FIG. 7a

CARDIAC TREATMENT DEVICES AND METHODS

CROSS-REFERENCES TO RELATED APPLICATIONS

The present application is a continuation-in-part application which claims priority to U.S. patent application Ser. No. 10/272,446, which was filed Oct. 15, 2002, now U.S. Pat. No. 6,849,075, which claims priority to U.S. Provisional Patent Application Ser. No. 60/337,070, filed Dec. 4, 2001, entitled "Methods and Devices for the Least Invasive Cardiac Surgery of Atrial Fibrillation," and the entire contents of these applications are hereby incorporated by reference.

BACKGROUND OF THE INVENTION

The present invention relates generally to medical devices and methods. More specifically, the invention relates to devices and methods for ablating epicardial tissue to treat cardiac arrhythmias such as atrial fibrillation.

Atrial fibrillation (AF) is a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3% of those aged 50–59 to more than 7% of those aged 80 and over. AF is responsible up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be underprescribed for AF. Despite the fact that warfarin reduces stroke risk by 60% or more, only 40% of patients age 65–74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

Although cardiac ablation devices and methods are currently available, many advances may still be made to provide improved devices and methods for ablating-epicardial tissue to treat AF and other arrhythmias. For example, currently available devices can be difficult to position and secure on epicardial tissue to perform an ablation. Devices such as bipolar ablation clamps and others can ablate tissue only in very limited patterns, such as one or two straight lines. Ablation devices often have no means for shielding ablative energy, to avoid unwanted burning of tissues in the vicinity of the heart, such as the esophagus. Relatively few devices can be secured to epicardial tissue with sufficient force to allow for stabilization of the heart. And many ablation devices may not be introduced by minimally invasive means, thus requiring an open surgical procedure. Typically, therefore, current cardiac ablation procedures for AF treatment still require stopping the heart and using a cardiopulmonary bypass apparatus.

Therefore, a need exists for improved devices and methods for ablating epicardial tissue to treat AF and other cardiac arrhythmias. Preferably, such devices and methods would provide ablation adjacent to and/or encircling one or more pulmonary veins, to disrupt conduction pathways and thus partially or completely treat AF. Also preferably, such devices and methods would allow for minimally invasive ablation procedures, in some cases on a beating heart. Such devices might also provide additional advantages, such as advantageous ablation patterns, shielding of ablative energy and/or the like. At least some of these objectives will be met by the present invention.

BRIEF SUMMARY OF THE INVENTION

Devices and methods of the present invention provide for ablation of cardiac tissue for treating cardiac arrhythmias such as atrial fibrillation. Although the devices and methods are often used to ablate epicardial tissue in the vicinity of at least one pulmonary vein, various embodiments may be used to ablate other cardiac tissues in other locations on a heart. Generally, devices of the invention include a tissue contacting member for contacting a portion of the epicardial tissue of a heart and securing the ablation device to the epicardial tissue, and an ablation member for ablating at least a portion of the tissue. In various embodiments, the devices have features which enable the device to attach to the epicardial surface with sufficient strength to allow the tissue to be stabilized via the device. For example, some embodiments may be used to stabilize a beating heart to enable a beating heart ablation procedure. Many of the devices may be introduced into a patient via minimally invasive incisions, introducer devices and the like. Although much of the following description focuses on using devices and methods of the invention to treat atrial fibrillation (AF) by ablating epicardial tissue on a human heart, the devices and methods may be used in veterinary or research contexts, to treat various heart conditions other than atrial fibrillation and/or to ablate cardiac tissue other than the epicardium.

In one aspect, a system for treating heart tissue to treat a cardiac arrhythmia comprises: at least one energy transmission member for applying energy to the heart tissue in a pattern to treat the cardiac arrhythmia; at least one tissue securing member coupled with the at least one energy transmission member for enhancing contact of the energy transmission member with the heart tissue; and at least one guiding member coupled with at least one of the energy transmission member and the tissue securing member for guiding the energy transmission member and the tissue securing member to a location for treating the heart tissue.

Optionally, such as system may further include at least one visualization member for enhancing visualization of the heart tissue and the treatment location. In some embodiments, for example, the visualization member may include an optic imaging device, a thermal imaging device, an ultrasound device, an electrical imaging device, a Doppler imaging device or the like, though any suitable device may be used. In some embodiments, an optic imaging device comprises a fiber optic device positionable to view a posterior portion of the heart tissue. In other embodiments, a thermal imaging device measures at least one heat transfer coefficient of the heart tissue to determine at least one of a type and a thickness of the heart tissue. In still other embodiments, an electrical imaging device measures electrical resistance and/or impedance of the heart tissue to determine a type and/or a thickness of the heart tissue.

In some embodiments, the at least one visualization member is removably coupled with at least one of the at least one energy transmission member, the at least one tissue securing member and the at least one guiding member. Also in some embodiments, the at least one visualization member may comprise at least one optic member for acquiring optic signals of an area to be visualized, and wherein the visualization member includes at least one inflatable member coupled with the visualization member at or near the optic member. For example, the inflatable member may provide a space in a body cavity and/or between at least two body tissues to enhance operation of the optic member. In some embodiments, the inflatable member includes an inflation port in fluid communication with an inflation lumen coupled with the visualization member for allowing introduction of a liquid or a gas to inflate the inflatable member. In some embodiments, the inflatable member reduces motion of the heart tissue when applied to the heart tissue.

Some embodiments of the invention also include at least one positioning device for contacting the heart tissue and positioning the heart tissue for treatment. For example, the positioning device may comprise a suction positioning device. In some embodiments, the positioning device reduces motion of a beating heart to further position the heart tissue for treatment.

The energy applied to the heart tissue may be any suitable energy, such as but not limited to radio frequency energy, ultrasound energy, microwave energy, cryogenic energy, thermoelectric energy and laser energy. In some embodiments, optionally, the energy transmission member contacts an epicardial surface of the heart tissue to transmit the energy, and wherein the energy is transmitted from the epicardial surface through the heart tissue to an endocardial surface. Sometimes, the energy is further transmitted through at least one of fat and connective tissue covering at least part of the epicardial surface. Some embodiments also include at least one grounding device for dispersing the energy from a patient undergoing an energy transmission heart procedure. Some embodiments may also include at least one needle coupled with the energy transmission member for insertion into the heart tissue to enhance the application of energy to the heart tissue. In some of these embodiments, the energy is transmitted from a tip of each needle. Optionally, the needle may be retractable. In some embodiments, for example, the retractable needle is exposed and retracted via a pneumatic member coupled with the energy transmission member. In some embodiments, the retractable needle is exposed and retracted automatically when the energy transmission member contacts the heart tissue. Also in some embodiments, the depth of penetration of the retractable needle into the heart tissue is adjustable.

Some embodiments may also include at least one closed circuit feedback loop for measuring and regulating operation of the energy transmission member. In some embodiments, either the energy transmission member or the tissue securing member further comprises at least one fluid aperture for applying fluid to the heart tissue to enhance the application of energy to the heart tissue.

In some embodiments, the energy transmission member is coupled with at least one guiding member such that a change in shape of the guiding member causes a corresponding change in shape of the energy transmission member. For example, the guiding member may comprise a deformable linear member its shape being adjustable by a user, and wherein the energy transmission member comprises a deformable linear member coaxially coupled with the guiding member so as to move with the guiding member. In some embodiments, the guiding member is adjustable to at least partially encircle at least one pulmonary vein.

In some embodiments, the tissue securing member includes at least one connector for removably coupling with the at least one energy transmission member. Sometimes, the tissue securing member is conformable to a surface topography of the heart tissue. In various embodiments, a first longitudinal axis of the tissue securing member and a second longitudinal axis of the removably coupled energy transmission member may be collinear, parallel to one another or offset from one another. In some embodiments, the energy transmission member comprises a linear member, and the connector comprises a plurality of connectors disposed along a length of the tissue securing member for removably coupling the linear member with the tissue securing member. The tissue securing member may allow compressive force to be applied between the at least one energy transmission member and the heart tissue.

In some embodiments, the tissue securing member comprises at least one vacuum applying member. The vacuum applying member may comprise, for example: at least one vacuum lumen; at least one vacuum port in fluid communication with the lumen for coupling the lumen with a vacuum source; and at least one aperture in fluid communication with the lumen for applying vacuum force to the heart tissue. In some embodiments, the vacuum lumen comprises multiple, separate lumens, and each separate lumen is in fluid communication with a separate vacuum port. Such embodiments may optionally further include means for selectively applying vacuum to one or more of the separate lumens without applying vacuum to one or more other separate lumens.

In other embodiments, the tissue securing member comprises at least one expansible balloon member. The expansible balloon member may include at least one fluid introduction port for allowing introduction of a liquid or a gas to expand the balloon member. Some embodiments include multiple, separate balloon members, wherein each separate balloon member is in fluid communication with a separate fluid introduction port. Such embodiments may also include means for selectively introducing fluid into one or more of the separate balloons without introducing fluid into one or more other separate balloons. Optionally, in some embodiments, the tissue securing member prevents a portion of the heart tissue from being treated by the at least one energy transmission member. For example, the tissue securing member may comprise at least one insulation material for preventing the portion of the heart tissue from being treated. In one embodiment, the insulation material further prevents the at least one energy transmission member from contacting or harming other, non-cardiac tissue of the patient and from contacting or harming a user of the energy transmission member.

In some embodiments, the guiding member comprises at least one of an elongate shaft, a steerable guidewire and an introducer sheath. For example, the steerable guidewire may comprise a pushable guidewire having at least one relatively stiff portion and one relatively flexible portion for positioning the energy transmission member in a location for treatment. For example, the steerable guidewire may comprise a pullable guidewire to which tension is applied to steer the guidewire to position the energy transmission member in a location for treatment.

In another aspect, a system for treating heart tissue to treat a cardiac arrhythmia comprises: at least one therapeutic agent transmission member for applying at least one therapeutic agent to the heart tissue in a pattern to treat the cardiac arrhythmia; at least one tissue securing member coupled with the at least one energy transmission member for enhancing contact of the energy transmission member with the heart tissue; and at least one guiding member coupled with at least one of the energy transmission member and the tissue securing member for guiding the energy transmission member and the tissue securing member to a location for treating the heart tissue. In some embodiments, for example, the therapeutic agent transmission member comprises at least one lumen and at least one aperture in the lumen for allowing passage of the at least one therapeutic agent out of the lumen to contact the heart tissue.

Optionally, such a system may further include at least one needle coupled with the therapeutic agent transmission member for insertion into the heart tissue to enhance application of the at least one therapeutic agent to the heart tissue. The therapeutic agent transmission member itself may comprise at least one needle and at least one aperture adjacent a tip of each needle for allowing passage of the at least one therapeutic agent out of the needle to contact the heart tissue. Optionally, the needle may be retractable. For example, the retractable needle may be exposed and retracted via a pneumatic member coupled with the therapeutic agent transmission member. In some embodiments, the retractable needle is exposed and retracted automatically when the therapeutic agent transmission member contacts the heart tissue. Also in some embodiments, a depth of penetration of the retractable needle into the heart tissue is adjustable.

In another aspect of the invention, a method for treating heart tissue of a patient to treat a cardiac arrhythmia involves: advancing at least one treatment member coupled with at least one tissue securing member through an incision on the patient; visualizing a treatment area in the patient with at least one visualization member; contacting the heart tissue of the patient with the treatment member and the tissue securing member; applying a force, through the tissue securing member, to enhance contact of the treatment member with the heart tissue; and treating the heart tissue, using the at least one treatment member. In some embodiments, the treatment member and/or the tissue securing member are advanced through a port applied to the patient, the port having a diameter no greater than 5 cm.

In some embodiments, the advancing step includes guiding the treatment member and/or the tissue securing member using at least one guiding member. Guiding may involve, for example, using a pushable guidewire having at least one relatively stiff portion and one relatively flexible portion for positioning the treatment member in a location for treatment. Alternatively, guiding may involve using a pullable guidewire to which tension is applied to steer the guidewire to position the treatment member in a location for treatment.

Some embodiments of the method further include using at least one positioning device to position the heart tissue for treatment. This may involve, for example, applying suction to the heart tissue. In some embodiments, using the positioning device reduces motion of the heart tissue. In other embodiments, contacting the heart tissue comprises applying a suction force with the tissue securing member to increase a contact surface area of the tissue securing member with the heart tissue. Applying the suction force may further comprise providing consistent contact force between the heart tissue and the tissue securing member. Optionally, applying the suction force may comprise securing the tissue securing member and the treatment member to the heart tissue, the tissue securing member and the treatment member having the same cross-sectional shape.

In some embodiments, treating the heart tissue comprises applying energy to the heart tissue in a pattern to reduce or eliminate the cardiac arrhythmia. The applied energy may be in any suitable form, such as radio frequency energy, ultrasound energy, microwave energy, cryogenic energy, thermoelectric energy or laser energy. In some embodiments, the energy is applied to an epicardial surface of the heart, wherein the energy is transmitted from the epicardial surface through the heart tissue to an endocardial surface. Optionally, the energy may be further transmitted through fat and/or connective tissue covering at least part of the epicardial surface. Some methods may further include dispersing the energy from the patient through at least one grounding device coupled with the patient.

Some embodiments further involve inserting at least one needle into the heart tissue to enhance the application of energy to the heart tissue. For example, the energy may transmitted from a tip of each needle. Some methods include extending the at least one needle from a retracted position before applying the energy and retracting the at least one needle to the retracted position when the energy has been applied. Such methods may also include selecting a depth of penetration of the at least one retractable needle into the heart tissue. Other embodiments may involve measuring the application of energy to the heart tissue using at least one closed circuit feedback loop and regulating the application of energy to the heart tissue based on the measurement. Still other embodiments may include applying fluid to the heart tissue to enhance the application of energy to the heart tissue.

In alternative embodiments, treating the heart tissue comprises applying at least one therapeutic agent to the heart tissue in a pattern to reduce or eliminate the cardiac arrhythmia. For example, applying the at least one therapeutic agent may involve infusing the agent through at least one aperture in the at least one treatment member. In some embodiments, the therapeutic agent is infused through at least one aperture in at least one needle coupled with the treatment member. In some embodiments, applying the at least one therapeutic agent comprises inserting at least one needle into the heart tissue to a desired depth, injecting the at least one agent into the heart tissue, and removing the at least one needle from the heart tissue. Such a method may further include extending the at least one needle from a retracted position for insertion into the heart tissue and retracting the at least one needle to the retracted position after injection.

Yet another embodiment may include adjusting a shape of a guiding member coupled with the at least one treatment member to alter the shape of the treatment member. In some embodiments, adjusting the shape of the guiding member allows the treatment member to conform to a surface of the heart tissue. Also in some embodiments, adjusting the shape of the guiding member allows the treatment member to at least partially encircle at least one pulmonary vein. Some embodiments may also include removably coupling the tissue securing member with the at least one treatment member. Some embodiments may further include conforming the tissue securing member to a surface topography of the heart tissue.

In some embodiments, applying force comprises applying compressive force between the at least one treatment member and the heart tissue. Applying the compressive force, in turn, may comprises applying vacuum force via at least one vacuum member of the tissue securing member. Such methods may further involve applying the vacuum force through at least a portion of the vacuum member while not applying the vacuum force through at least another portion of the vacuum member. In some embodiments, applying the compressive force comprises applying force via at least one expansible balloon member. A method may further comprising preventing, using the tissue securing member, a portion of the heart tissue from being treated by the at least one treatment member. For example, the tissue securing member may comprise at least one insulation material for preventing the portion of the heart tissue from being treated.

In some embodiments, visualizing comprises using at least one visualization member selected from the group consisting of an optic imaging device, a thermal imaging device, an ultrasound device, an electrical imaging device and a Doppler imaging device. Some embodiments also include expanding an expansible balloon coupled with the visualization member near an optic element to enhance visualization. Sometimes, expanding the balloon provides a space in a body cavity and/or between at least two body tissues to enhance operation of the optic member. Optionally, expanding the balloon may reduce motion of the heart tissue when applied to the heart tissue.

In yet another aspect, a method for treating heart tissue of a patient to treat a cardiac arrhythmia comprises: advancing at least one treatment member and at least one tissue securing member through an incision on the patient; removably coupling the at least one treatment member with the at least one tissue securing member; visualizing a treatment area in the patient with at least one visualization member; contacting the heart tissue of the patient with the treatment member and the tissue securing member; applying a force, through the tissue securing member, to enhance contact of the treatment member with the heart tissue; and treating the heart tissue, using the at least one treatment member. In some embodiments, and treatment member is advanced through the tissue securing member. Optionally, in some embodiments, the treatment member and the tissue securing member are advanced through a minimally invasive port applied to the patient.

Various embodiments of the devices and methods described briefly above are further described in the appended drawings and the following detailed description. The description of specific embodiments is provided for exemplary purposes and should not be interpreted to narrow the scope of the invention as defined in the claims.

BRIEF DESCRIPTION OF THE DRAWINGS

FIG. 7 is a perspective view of an elongate shaft ablation device, according to one embodiment of the invention.

FIG. 7a is a perspective view of the distal end of a shaft as in FIG. 6, with straight jaws, according to one embodiment of the invention.

DETAILED DESCRIPTION OF THE INVENTION

The present invention relates generally to medical devices and methods and more specifically to devices and methods for ablating cardiac tissue for treating cardiac arrhythmias such as atrial fibrillation. Ablation of cardiac tissue in various patterns has been shown to disrupt conduction pathways in the heart to ameliorate or eliminate AF or other arrhythmias. The devices and methods will often be used to ablate epicardial tissue in the vicinity of at least one pulmonary vein, but various embodiments may be used to ablate other cardiac tissues in other locations on a heart.

Generally, ablation devices of the invention include at least one tissue contacting member for contacting a portion of the epicardial tissue of a heart, securing means for securing the ablation device to the tissue and at least one ablation member coupled with the contacting member for ablating at least a portion of the tissue. In various embodiments, the devices have features which enable the device to attach to the epicardial surface with sufficient strength to allow the tissue to be stabilized via the device. For example, some embodiments may use suction force to secure the device to epicardial tissue and stabilize a beating heart to enable a beating heart ablation procedure. Other embodiments may include other optional features, such as sensors for sensing whether tissue has been ablated, a support member with an arm for connecting the device to a positioning device, cooling apparatus for cooling epicardial tissue, visualization devices and/or the like. Some embodiments of the device are introducible into a patient via minimally invasive means, such as a minimally invasive incision, sheath, trocar or the like.

Methods of the invention generally include contacting a device with epicardial tissue, using a tissue contacting member on the device to secure the device to the tissue, and ablating the tissue with an ablation member on the device. In some embodiments, the method further includes additional steps such as positioning the device on the epicardial tissue, stabilizing cardiac tissue, cooling cardiac tissue, positioning the device using a positioning device, visualizing epicardial tissue with an imaging device and/or the like. Again, although much of the following description focuses on embodiments used to treat AF by ablating epicardial tissue near one or more pulmonary veins on a human heart, the devices and methods may be used in veterinary or research contexts, to treat various heart conditions other than AF, to ablate cardiac tissue other than the epicardium and/or in any other suitable manner or context.

Figure 1:
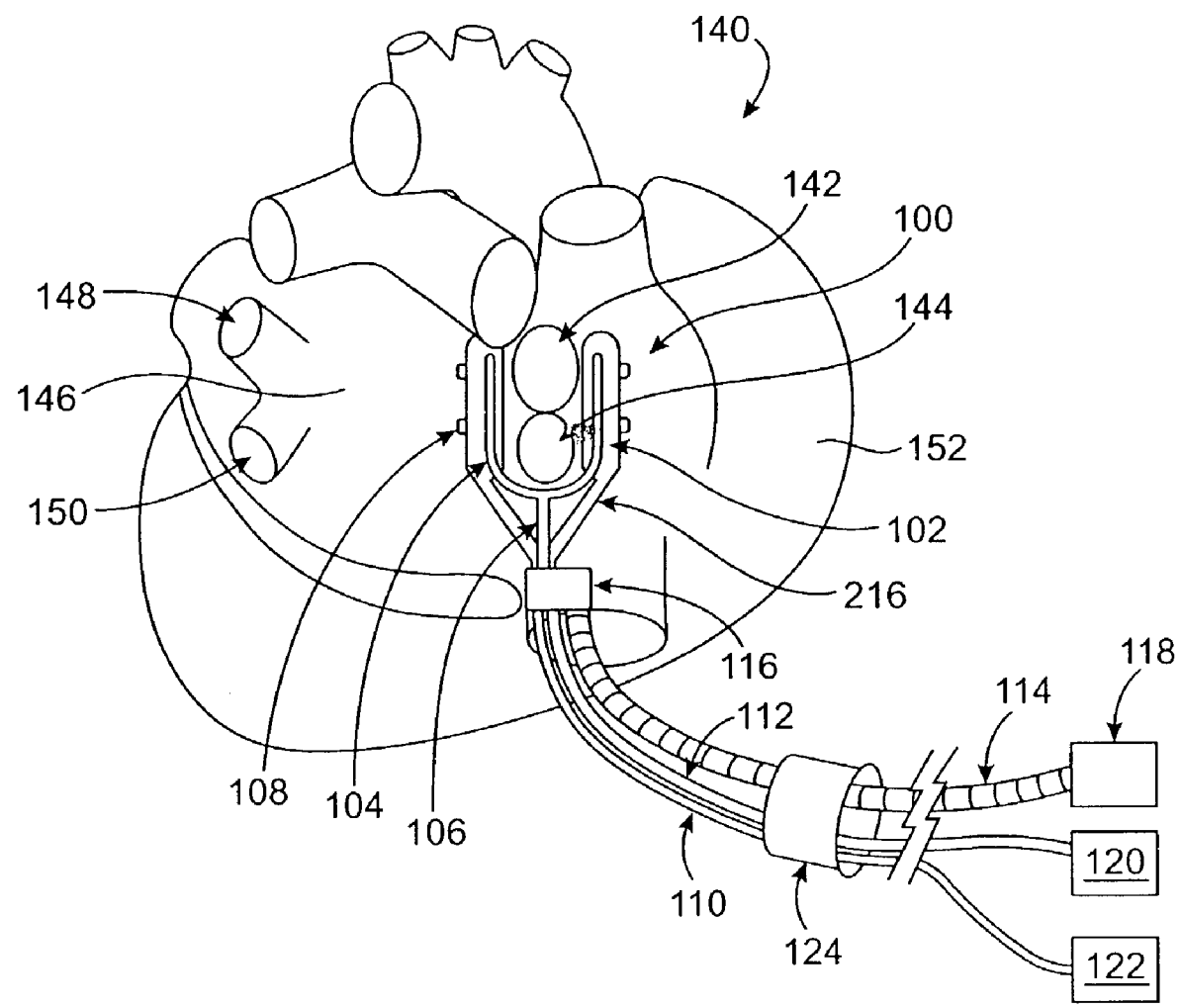
FIG. 1 is a perspective view illustration of a human heart and an ablation device in position for performing an ablation procedure, according to one embodiment of the invention.

Referring now to FIG. 1, an ablation device 100 is shown in position for ablating epicardial tissue on a human heart 140. A top view of ablation device 100 is shown, the visible components of device 100 including a tissue contacting member 102 coupled with a suction connector 216 and a support member 104 having a support arm 106. Tissue contacting member 102 also includes multiple artery securing arms 108 for securing one or more coronary arteries. Suction connector 216 is coupled with a suction cannula 112, which in turn is coupled with a suction source 120. Support arm 106 is coupled via a clamp 116 to a positioner 114, which in turn is coupled to a stabilizing device 118 for stabilizing positioner 114. Finally, an ablation member (not visible) of ablation device 100 is coupled, via a wire 110, to an energy source 122. In various embodiments, ablation device 100 may be introduced into a patient through a minimally invasive introducer device, such as a sheath 124, trocar or the like, as is represented in FIG. 1 by a simplified representation of sheath 124.

In FIG. 1, ablation device 100 is shown in a position partially encircling the right superior pulmonary vein 142 and the right inferior pulmonary vein 144. As will be described in further detail below, such a position is only one possible configuration for treating heart 140. In other embodiments, for example, both of the right pulmonary veins 142, 144 may be completely encircled, only one may be partially or completely encircled, the left superior 148 and/or left inferior 150 pulmonary veins may be partially or completely encircled and/or various patterns may be ablated on the left atrium 146, the right atrium 152 and/or the right and left ventricles (not labeled). Any ablation pattern suitable for heart treatment may be accomplished by one or more embodiments of the present invention. Thus, the following descriptions of various embodiments should not be interpreted to narrow the scope of the invention as set forth in the claims.

Generally, ablation device 100 includes at least one tissue contacting member 102 coupled with at least one ablation member (not shown in FIG. 1). One embodiment of a device which may be used as tissue contacting member 102 is described in U.S. Patent Application Ser. No. 60/182,048, filed on Feb. 11, 2000, the entire contents of which is hereby incorporated by reference. Ablation device 100 shown in FIG. 1 actually includes two tissue contacting members 102, one on either side of the right pulmonary veins 142, 144. Tissue contacting members 102 may be coupled together via support member 104 and suction connector 216. In other embodiments, some of which will be described below, tissue contacting member 102 may include only one member, more than two members, a coupling member disposed between multiple arms and/or the like. Alternatively, tissue contacting member 102 may be conical, linear, shaped as a flat pad or a flat elongate member or may have any other suitable configuration. Additionally, tissue contacting members 102 may have any suitable size and dimensions. For example, in FIG. 1, tissue contacting members 102 and device 100 in general have a shape and dimensions to contact and ablate epicardial tissue on heart 140 in a pattern partial encircling the right pulmonary veins 142, 144. Many other configurations and sizes are possible, as described further below.

Tissue contacting members 102 may be manufactured from any suitable material, such as a polymer, plastic, ceramic, a combination of materials or the like. In one embodiment, for example, tissue contacting members 102 are manufactured from a liquid molded silicone rubber. In some embodiments, the material used to make tissue contacting members 102 is chosen to allow the members 102 to be at least partially deformable or malleable. Deformable tissue contacting members 102 may allow ablation device 100 to be inserted into a patient and/or advanced to a surgical site within the patient via a minimally invasive incision or a minimally invasive introducer device, such as sheath 124. Deformable tissue contacting members 102 may also allow device 100 to conform to a surface of heart 140, to enhance ablation of epicardial or other cardiac tissue. In some embodiments, tissue contacting members 102 include one or more artery securing arms 108, for securing, exposing and/or occluding one or more coronary arteries via silastic tubing attached between the artery and securing arm 108. Securing arms 108 are generally made of the same material(s) as tissue contacting members 102 but may also suitably comprise other materials.

In some embodiments, tissue contacting members 102 are coupled with support member 104. Support member 104 may be made of any suitable biocompatible material, such as titanium, stainless steel, nickel titanium alloy (Nitinol) or the like. Support member 104 may be coupled with tissue contacting members 102 by any suitable means, such as but not limited to one or more adhesive substances, placement of a portion of support member 104 within a sleeve on tissue contacting members 102 or a combination of both. Like tissue contacting members 102, support member 104 may also be malleable or deformable to allow for insertion of ablation device 100 through a minimally invasive sheath 124 and/or for enhancing conformability of device 100 to a surface of heart 140. Support member 104 typically includes at least one support arm 106 or similar protrusion or multiple protrusions for removably coupling ablation device 100 with positioner 114 or one or more other positioning devices. Positioner 114, for example, may comprise a flexible, positioning arm, with attachment means such as clamp 116 for attaching to support arm 106 and stabilizing device 118 for stabilizing positioner 114. For example, a flexible, articulating positioner 114 may be of the type which rigidities when tensile force is applied, such as via a tensioning wire. Any other suitable positioner 114 may alternatively be used. In other embodiments, device 100 may not include support member 104. Such devices 100 may incorporate a connection arm onto a tissue contacting member 102, may be positioned on heart 140 using a positioning device inserted through a separate incision, or may be positioned or manipulated by a physician or other user via any other suitable means.

Tissue contacting members 102 may also be coupled with one or more suction cannulas 112 to provide suction for enhancing contact of ablation device 100 with epicardial tissue. In various embodiments, tissue contacting members 102 may be directly coupled to one or more cannulas 112 or may be connected via one or more suction connectors 216. In FIG. 1, a V-shaped suction connector is used to couple the two tissue contacting members 102 with a common cannula 112. Cannula 112, in turn, is connected to suction source 120, which may be a conventional wall suction or stand-alone suction source. Generally, cannula 112 may be any suitable conventional cannula 112, which are well known to those skilled in the art. Suction connector 216 is typically comprised of the same material(s) as tissue contacting members 102, but may also be made of a material or materials used to make cannula 112. Suction connector 216 may further include a nozzle 218 (FIG. 2) for connecting to cannula 112.

Figure 2:
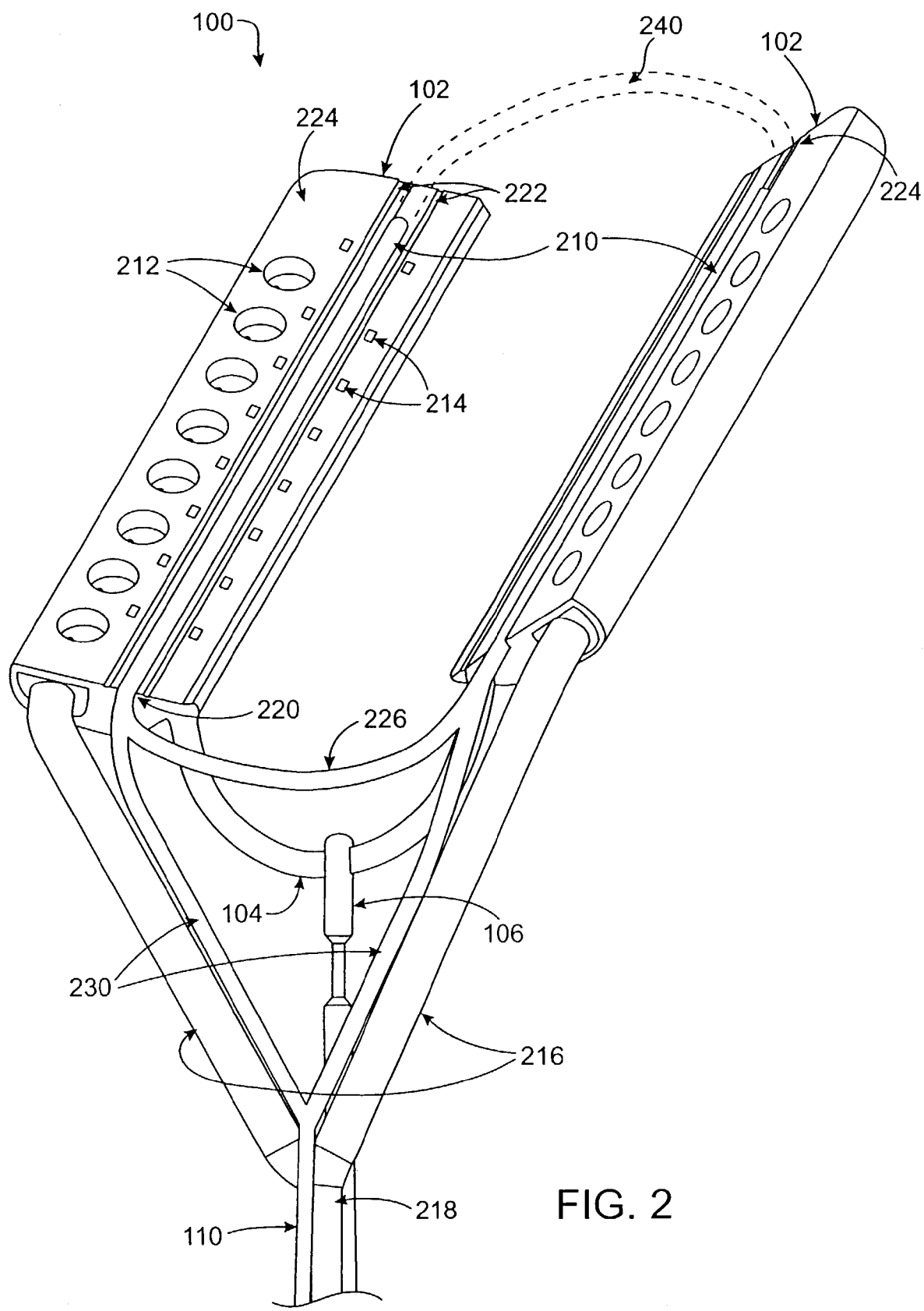
FIG. 2 is a perspective view of an ablation device, according to one embodiment of the invention.

Ablation device 100 also includes at least one ablation member 210 (FIG. 2). Ablation member 210 typically receives energy from a separate energy source 122, although ablation members 210 with internal energy sources are also contemplated. Where a separate energy source 122 is used, ablation member 210 may be coupled with source 122 by any suitable means. In one embodiment, for example, ablation member 210 may be coupled to energy source 122 with wire 110. Wire 110 may be any suitable connector, such as fiber optic cable, electric cable, coaxial cable, ultrasound transmission device or the like. As is described further below, any suitable energy may be provided by energy source 122 for ablation and any means for transmitting energy to ablation member 210 is contemplated within the scope of the invention. In some embodiments, for example, energy may be transmitted remotely, so that no wires or other similar connecting devices are required. In other embodiments, radio frequency energy may be provided by an RF energy source and transmitted to ablation member 210 via conventional electrical wire(s) 110.

Generally, ablation member 210 may be configured to transmit energy of any suitable quantity or force. For example, in some embodiments sufficient energy will be transmitted through ablation member 210 to ablate only epicardial tissue on a heart. In other embodiments, sufficient energy may be transmitted to cause one or more layers beneath the epicardial tissue to be ablated. In some embodiments, for example, one or more transmural lesions (across the entire wall of the heart) may be ablated. Typically, an amount of energy transmitted through ablation member 210 will be adjustable to create an desired ablation depth.

As mentioned briefly above, a minimally invasive introducer sheath 124, trocar or other minimally invasive device may be used for introducing one or more of the components shown in FIG. 1 into a patient. In some embodiments, a sheath need not be used and instead only a minimally invasive incision is used. In other embodiments, multiple minimally invasive incisions and/or sheaths 124 may be used for introducing various devices into a patient. For example, one sheath 124 may be used for introducing ablation device 100 and another sheath 124 may be used for introducing positioner 114. Although devices and methods of the present invention are often suitable for minimally invasive procedures, they may also typically be used in open surgical procedures, either with or without cardiopulmonary bypass, in various embodiments.

Referring now to FIG. 2, an embodiment of ablation device 100 is shown in further detail. Device 100 is shown from a bottom/angled view to show a tissue contacting surfaces 224 of tissue contacting members 102, ablation member 210, suction apertures 212 and sensors 214. Like tissue contacting members 102, tissue contacting surfaces 224 may be given any configuration and sizes to contact cardiac tissue in an area around the tissue to be ablated. For example, in an embodiment as in FIG. 2 a tissue contacting surface 224 on one tissue contacting member 102 may have a length of approximately 1.25 in. and a width of approximately 0.5 in., with a space between the two tissue contacting surfaces measuring approximately 0.4 in. Such exemplary dimensions are in no way limiting, and all combinations of dimensions for one or more tissue contacting members 102 are contemplated. In some embodiments, as in FIG. 2, surfaces 224 may be flat and smooth. In other embodiments, surfaces 224 are textured, curvilinear or otherwise shaped to enhance contact of tissue contacting members 102 with heart 140. Some embodiments may further include one or more surface features 222. Such features 222 may enhance friction between tissue contacting surfaces 224 and epicardial tissue and/or may provide an area for placement of additional features, such as irrigation apertures for cooling tissue or the like.

Ablation member 210 may include one or more ablation members for transmitting one or more of a variety of ablation agents to epicardium or other cardiac tissue. In some embodiments, as commonly shown in the drawing figures, ablation member 210 may comprise a single, continuous, RF ablation coil or wire for transmitting RF energy to cardiac tissue. In other embodiments, ablation member 210 may be multiple radio frequency devices or one or more cryogenic devices, ultrasound devices, laser devices, thermo-electric chip devices, chemical agent delivery devices, biological agent delivery devices, light-activated agent devices, thermal devices, microwave devices, or ablating drug delivery devices. Other suitable ablation devices are also contemplated within the scope of the invention.

Additionally, radio frequency ablation members 210 may be bipolar or unipolar in various embodiments. In conjunction with any of these various embodiments, energy source 122 may provide any of the above-listed types of ablative energy or substance, any combination thereof or any other suitable ablative energy or substance.

Ablation member 210 may be given any configuration or size for ablating cardiac tissue. In the embodiment shown in FIG. 2, for example, ablation member 210 has two linear portions disposed along most of the lengths of contacting surfaces 224 of tissue contacting members 102, and the linear portions are continuous with a curved portion 226 so that ablation member 210 is generally U-shaped. Alternatively or additionally, ablation member 210 may continue proximally from tissue contacting members 102 in one or more arms 230 which eventually connect to wire 110 or other connective device. In some embodiments, curved portion 226 may be eliminated so that ablation member 210 comprises two linear ablation members connected to wire 110 via arms 230. In yet other embodiments, arms 230 may be eliminated and ablation member 210 may be coupled directly to wire 110 without interposing arms.

Generally, ablation members 210 and tissue contacting member 102 may have any shapes, sizes, configurations or combinations of shapes and sizes to produce a desired ablation pattern on epicardial or other tissue of a heart. In some examples, ablation members 210 and tissue contacting members 102 are configured to partially or completely encircle or surround one pulmonary vein. In other embodiments, they may be configured to partially or completely surround two pulmonary veins on the same side of the heart, such as the left superior and left inferior pulmonary veins. In still other embodiments, the right and left inferior pulmonary veins or the right and left superior pulmonary veins may be partially or wholly encircled. And in still other embodiments, all four pulmonary veins may be partially or completely encircled by ablation members 210 and tissue contacting member 102. Some of these embodiments are described in further detail below, but it should be understood that any possible configuration is contemplated within the scope of the present invention.

In some embodiments, all or a portion of ablation member 210 or tissue contacting member 102 may be steerable. Steerability means that an ablation member 210 or tissue contacting member 102 may be adjusted to fit around or next to one or more pulmonary veins or to otherwise assume a desired configuration. For example, some embodiments may include a pull wire coupled with ablation member 210 and/or tissue contacting member 102. The pull wire, when pulled, deflects ablation member 210 and/or tissue contacting member 102 to one side or around a curved structure. Other embodiments may include pushable wires, combinations of flexible and stiff portion and/or the like to provide steerability.

In some embodiments, for example, it is desirable to ablate epicardial tissue in a circumferential pattern around one or more pulmonary arteries. Various configurations of tissue contacting members 102 and ablation members 210 are contemplated for achieving such ablation patterns. For example, a retractable RF coil 240 or other retractable ablation device may be incorporated into or used in conjunction with ablation member 210 as shown in FIG. 2. Retractable coil 240 could be housed within tissue contacting member 102, for example, and could be released when desired to surround or encircled one or two pulmonary veins. As already described, the RF ablation member 210 and/or the RF retractable coil 240 pictured in FIG. 2 may be replaced, in other embodiments, with devices using radio frequency energy, ultrasound energy, microwave energy, cryogenic energy, thermoelectric energy or laser energy for ablating tissue. For example, ablation member 210 in some embodiments comprises multiple thermoelectric chips disposed in a pattern on tissue contacting members 102.

Although ablation device 100 and ablation member 210 are often shown as being generally U-shaped, many other configurations are possible. As described further below, a ablation device 100 may be conical in shape, with ablation member 210 being disposed in a circle at the base of the cone which contacts cardiac tissue. In other embodiments, device 100 may be configured as a flat patch and one or more linear or curvilinear ablation members 210 may be incorporated into the patch. For example, ablation device 100 may include a combination of multiple ablation members 210 to ablate a pattern on heart 140 such as: a first linear ablation member for contacting heart tissue between a left pulmonary vein and a right pulmonary vein; a second linear ablation member for contacting heart tissue at a location approximating a line extending to the atrioventricular groove; and a third linear ablation member for contacting heart tissue on a left atrial appendage. In such an embodiments, one or more of ablation members 210 may overlap one another. In some embodiments involving multiple ablation members 210, each member may be controllable on a separate radio frequency channel or other energy transmission channel.

Tissue contacting members 102 optionally include one or more attachment means for enhancing contact of ablation device 100 with epicardial or other cardiac tissue. In some embodiments, one or more suction apertures 212 are used. Each suction aperture 212 generally includes a depressed surface and a small suction hole. The suction hole is connected to a lumen (not shown) within tissue contacting member 102, and the lumen is then couplable with a suction cannula 122 or connector 216 for connecting to cannula 122. Suction apertures 212 may be given any suitable configuration, size or pattern. For example, suction holes may be disposed on tissue contacting member 102 is a largely linear pattern, as in FIG. 2. In other embodiments, suction apertures may be arranged in two parallel lines such that ablation member 210 is disposed between the two parallel lines of suction apertures 212. In still another embodiment, ablation device 100 may include one tissue contacting member 102 having a conical shape, with the base of the cone contacting epicardial tissue and the entire conical tissue contacting member 102 acting as one suction aperture.

In some embodiments, suction force may be applied via suction apertures 210 with sufficient strength to allow for stabilization and/or positioning of heart 140. For example, a physician may place ablation device 100 on a beating heart 140, apply suction, and hold heart 140 is a relatively stable or reduced-motion position while performing an ablation procedure. The physician may also (or alternatively) turn or otherwise move heart 140, using ablation device 100, such as when a different angle of heart 140 would be advantageous for viewing or treating a portion of heart 140. In these or other embodiments, suction force applied through suction apertures 212 may be of sufficient strength to dissect through one or more layers of adipose tissue covering epicardial tissue. Such dissection by suction apertures 212 may allow for improved contact of the epicardial tissue by device and, thus, improved ablation. In alternative embodiments, suction apertures 212 may be replaced or supplemented by other means for securing ablation device 100 to epicardial tissue. For example, an adhesive may be applied to tissue contacting surfaces 224. Such adhesives or other securing means may also be sufficiently strong, in some embodiments, to allow for positioning and/or stabilization of heart 140.

Tissue contacting members 102 may also include one or more sensors 214 for sensing when tissue has been ablated. Sensors 214 may include one or more thermal sensors, electrical sensors, thermoelectric sensors, microchips, thermistors, thermocouples and ultrasonic sensors. As shown in FIG. 2, some embodiments include two or more paired sensors 214, with one sensor of each pair on one side of ablation member 210 and the other sensor on the opposite side. In some embodiments, one sensor 214 transmits a signal through epicardial tissue to its paired sensor 214. If epicardial tissue between the two paired sensors 214 has been ablated, then energy will transmit poorly through that ablated tissue. Thus, the receiving sensor 214 will receive reduced or no energy transmitted from the transmitting sensor 214. If tissue between two paired sensors has not been ablated, the signal should travel through the tissue with only slight reduction in strength. By using such paired sensors 214 and comparing signals received in different pairs, areas of ablation can be compared, to determine if all desired areas for ablation have been sufficiently ablated. Other configurations one or more sensors 214 may also be used.

Figure 2A:
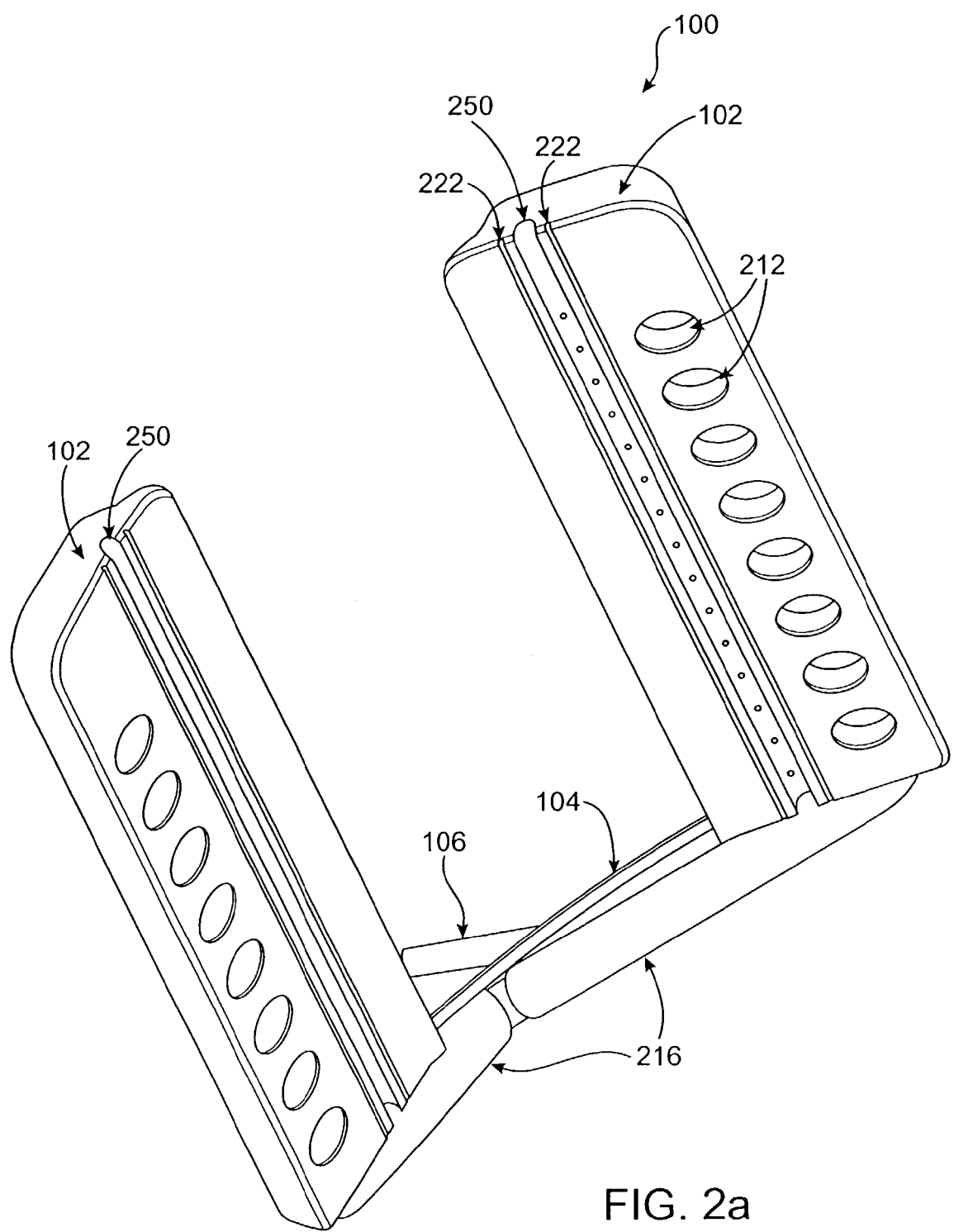
FIG. 2a is a perspective view of the ablation device shown in FIG. 2, with the ablation member removed.

Referring now to FIG. 2a, another view of ablation device 100 as in FIG. 2 is shown, with ablation member 210 removed for clarity. In some embodiments, tissue contacting members 102 include a linear trough 250 in which ablation member 210 is placed, either removably or permanently. Positioning ablation member 210 in trough 250 may provide improved contact between ablation member 210 and epicardial tissue while also providing ablation device 100 with durability. Surface features 222 are again shown in FIG. 2a. These features may simply enhance contact of tissue contacting members 102 with epicardial tissue or may also contain additional features, such as sensors, irrigation apertures for allowing passage of irrigation fluid for cooling ablated tissue, small suction apertures and/or the like.

Optionally, various embodiments of ablation device 100 may further include at least one cooling member for cooling a portion of ablated epicardial tissue, epicardial tissue surrounding an ablated area, other nearby tissues and/or a portion of device 100. Cooling members are not shown in the drawing figures, for purposes of clarity. Generally, a cooling member may comprise any suitable device for cooling a tissue. In some embodiments, cooling member includes at least one inlet port, for allowing introduction of a cooling substance into the member, a hollow internal cooling member, and at least one outlet port for allowing egress of the cooling substance. The cooling substance itself may be carbon dioxide, any other suitable gas, saline or any other suitable liquid. In some embodiments, the hollow cooling member comprises a tubular member disposed within tissue contacting member 102 in general proximity with ablation member 210. In other embodiments, cooling member may comprise a chamber for containing cooling substance or a series of irrigation holes for allowing cooling substance to flow out of tissue contacting member 102 to contact ablated or other epicardial tissue. Many other suitable cooling apparatus are contemplated for use within the scope of the present invention.

Figure 3:
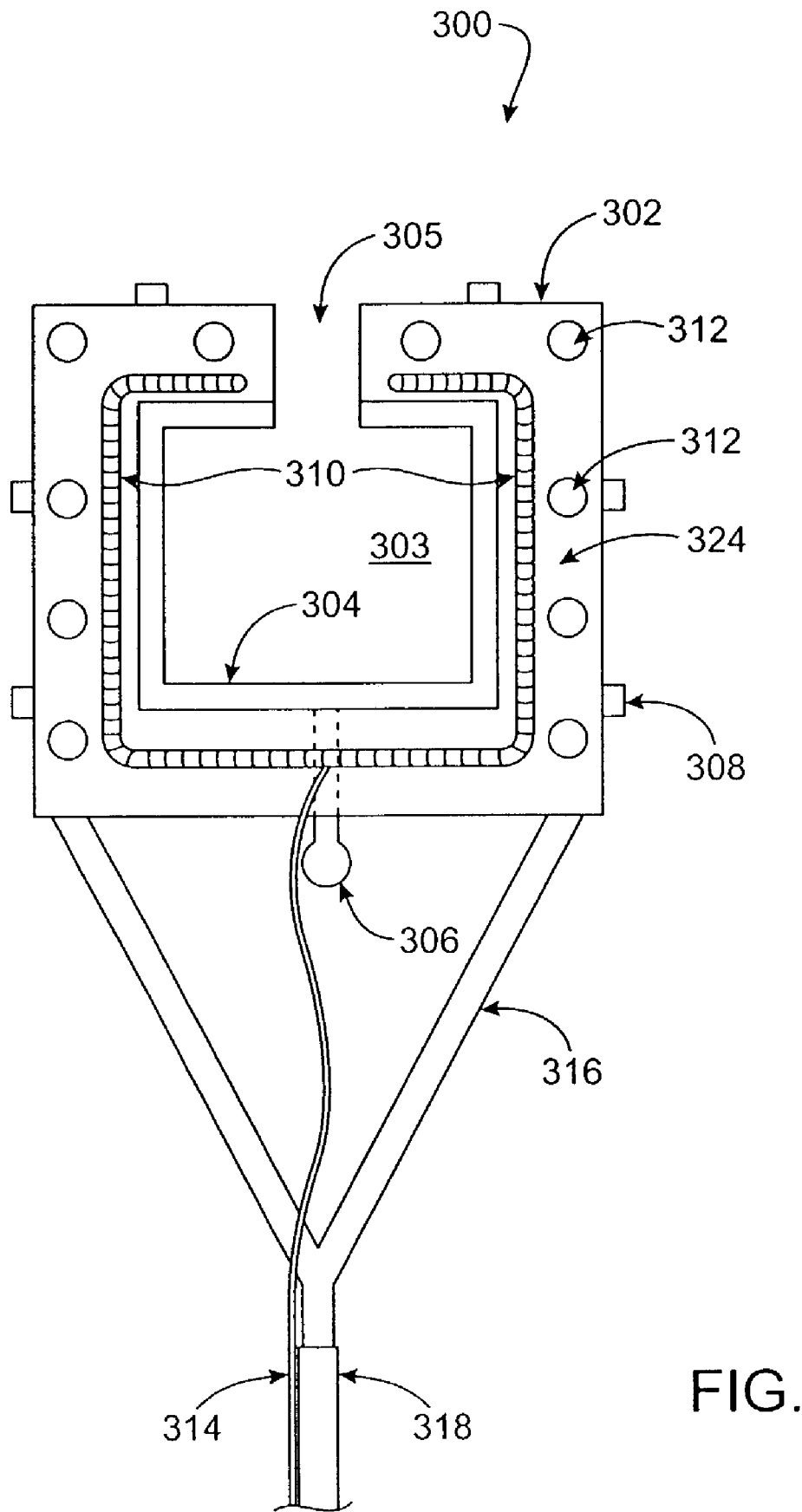
FIG. 3 is a bottom-surface view of an ablation device, according to one embodiment of the invention.

With reference now to FIG. 3, another embodiment of ablation device 300 is shown from a bottom-side view. Ablation device 300 includes a tissue contacting member 302, coupled with an ablation member 310 and a support member 304. As with some above-described embodiments, tissue contacting member includes a tissue contacting surface 324, tissue attaching means including multiple suction apertures 312 and multiple artery securing arms 308. Tissue contacting member 302 is removably couplable with a suction cannula 318 via a V-shaped suction connector 316. Ablation member 310 is coupled with energy transmitting wire 314 for coupling with an energy source (not shown). Support member 304 includes a support arm 306 (shown partially in dotted lines, since it extends on the opposite side of tissue contacting member 302) for coupling device 300 with a positioning device.

In ablation device 300, tissue contacting member 302, ablation member 310 and support member 304 are all generally shaped as a square with a central area 303 and a top area 305 left open. Such a configuration may be used, for example, to contact and ablate epicardial tissue almost completely encircling one or more pulmonary veins. Leaving top area 305 open may allow device 300 to be positioned around such veins or other vessels while still providing almost circumferential ablation. In other embodiments, either central area 303, top area 305 or both may be closed to provide for different contact and/or ablation patterns on epicardial tissue. In still other embodiments, one or more hinges may be positioned on ablation device 300 to allow top area 305 to be closed after positioning device 300 around one or two pulmonary veins. Again, any configuration, shape, size, dimensions or the like are contemplated within the scope of the invention.

Figure 4:
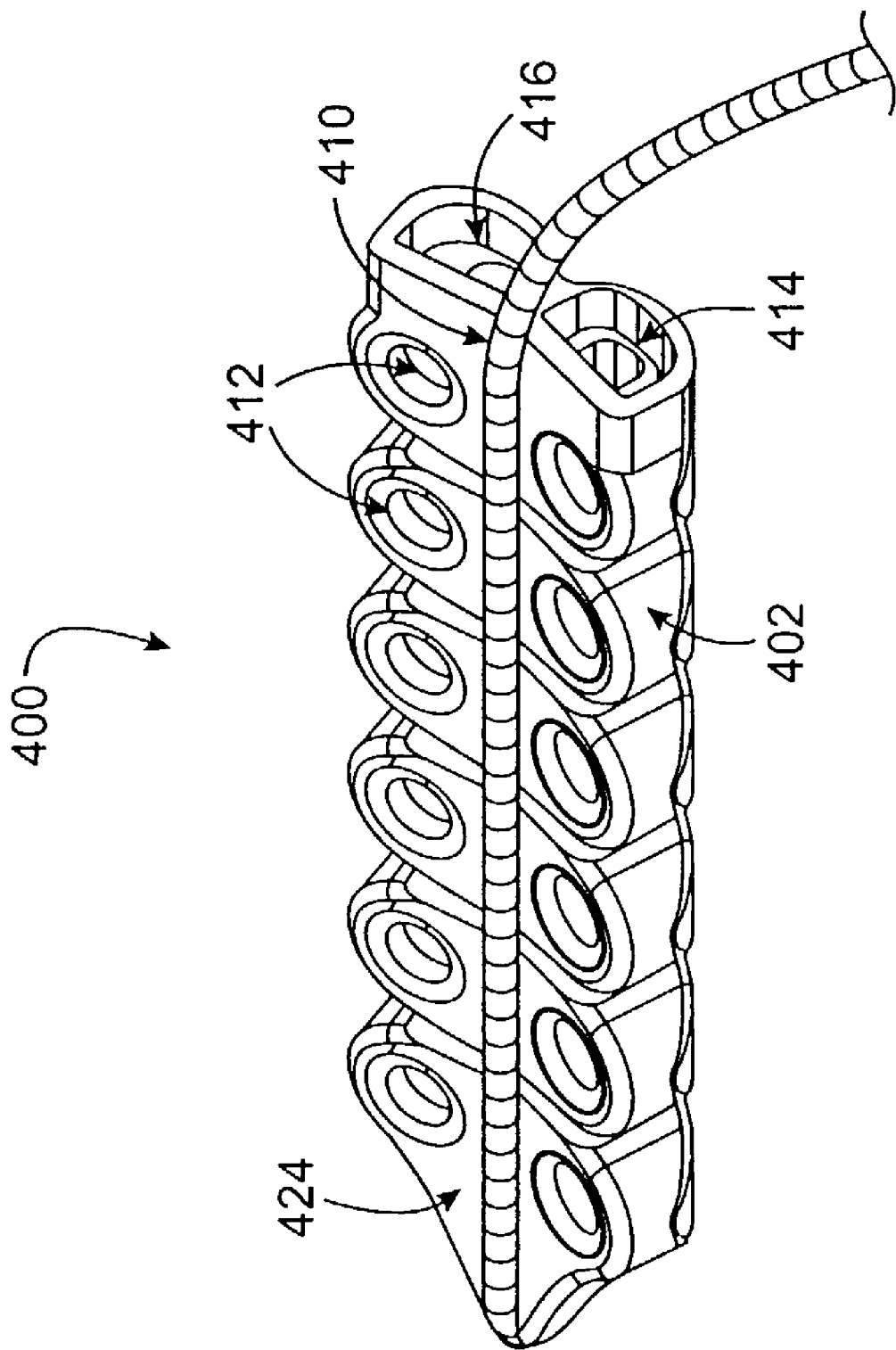
FIG. 4 is a perspective view of a flexible, elongate ablation device with two rows of suction apertures, according to one embodiment of the invention.

Referring now to FIG. 4, another embodiment of ablation device 400 comprises a largely flexible device which includes a tissue contacting member 402 and an ablation member 410. Tissue contacting member 402 may be made of any suitable, flexible material, such as a silicone, polyurethane, polycarbonate, another suitable polymer or combination of polymers or the like. Tissue contacting member 402 generally includes a tissue contacting surface 424 having multiple suction apertures 412. Tissue contacting surface 424 may be slightly concave (as shown), flat or may have any other suitable shape. Suction apertures 412 are disposed in two parallel lines, one line on either side of ablation member 410 and communicate with suction lumens 414 and 416. Suction lumens 414, 416 may be coupled with one or more suction cannulas or similar devices for providing suction force through suction apertures 412. Other embodiments may include one common suction lumen for connection to a suction cannula.

As with various embodiments described above, any suitable ablation means may be used as ablation member 410 in device 400. In the embodiment shown, ablation member 410 comprises a linear radio frequency coil. Ablation member 410 may extend beyond the length of tissue contacting member 402, either in a proximal or distal direction and may be coupled with a source of energy via a wire (not shown) or other connection device. In various embodiments, one or more of the features described above, such as support members, retractable ablation elements, sensors, cooling members, positioning arms and/or the like may be incorporated into or used with ablation device 400. Alternatively, ablation device 400 may simply include tissue contacting member 402 and linear ablation member 410. Such an embodiment may be advantageous for introduction through a narrow, minimally invasive introducer sheath, due to the device's flexibility and relatively small size. In one embodiment, for example, device 400 may measure approximately 3.25 in. in length and approximately 0.9 in. wide and may further be deformable to a narrower configuration for insertion through a sheath. Furthermore, device 400 may be sufficiently flexible to conform to curved surfaces of heart 140, allowing for enhanced contact with and ablation of epicardial tissue. Finally, it may sometimes be advantageous to ablate epicardial tissue in a linear pattern or in multiple line. Ablation device 400 may be movable, to allow ablation in a first line, a second line, a third line and/or the like.

Figure 4A:
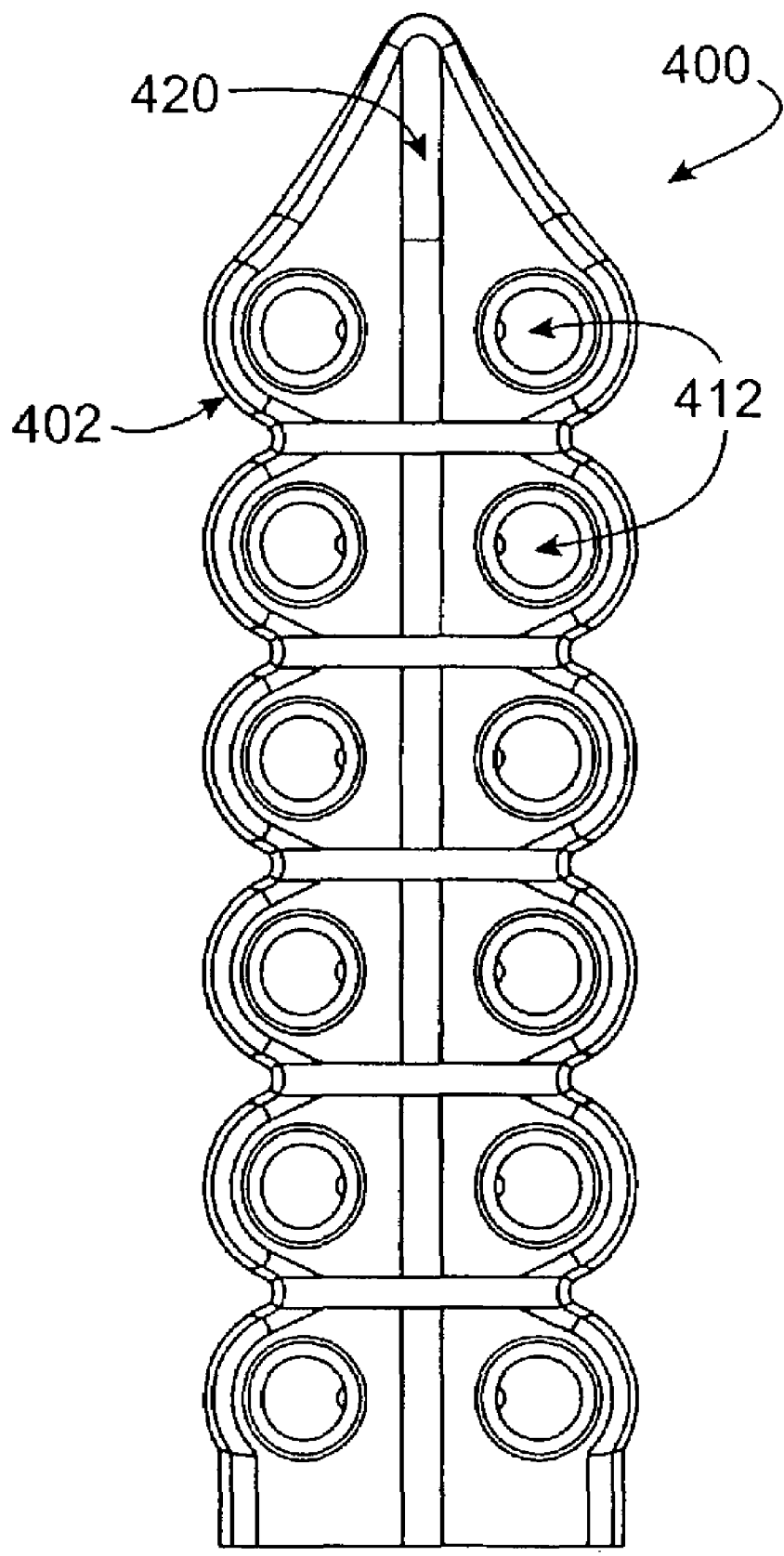
FIG. 4a is a bottom-surface view of the ablation device as shown in FIG. 4, with the ablation member removed.

Referring now to FIG. 4a, a bottom-side view of ablation device 400 is shown with ablation member removed. It can be seen that tissue contacting member 402 may include a trough 420 in which ablation member 410 may be positioned. In some embodiments, ablation member 410 may be a removable piece which may be removably attached to tissue contacting member 402, at least partially disposed within trough 420, so that one ablation member 410 may be used with multiple tissue contacting members 402, one after another, for example if tissue contacting members 402 are single-use, disposable devices.

Figure 5:
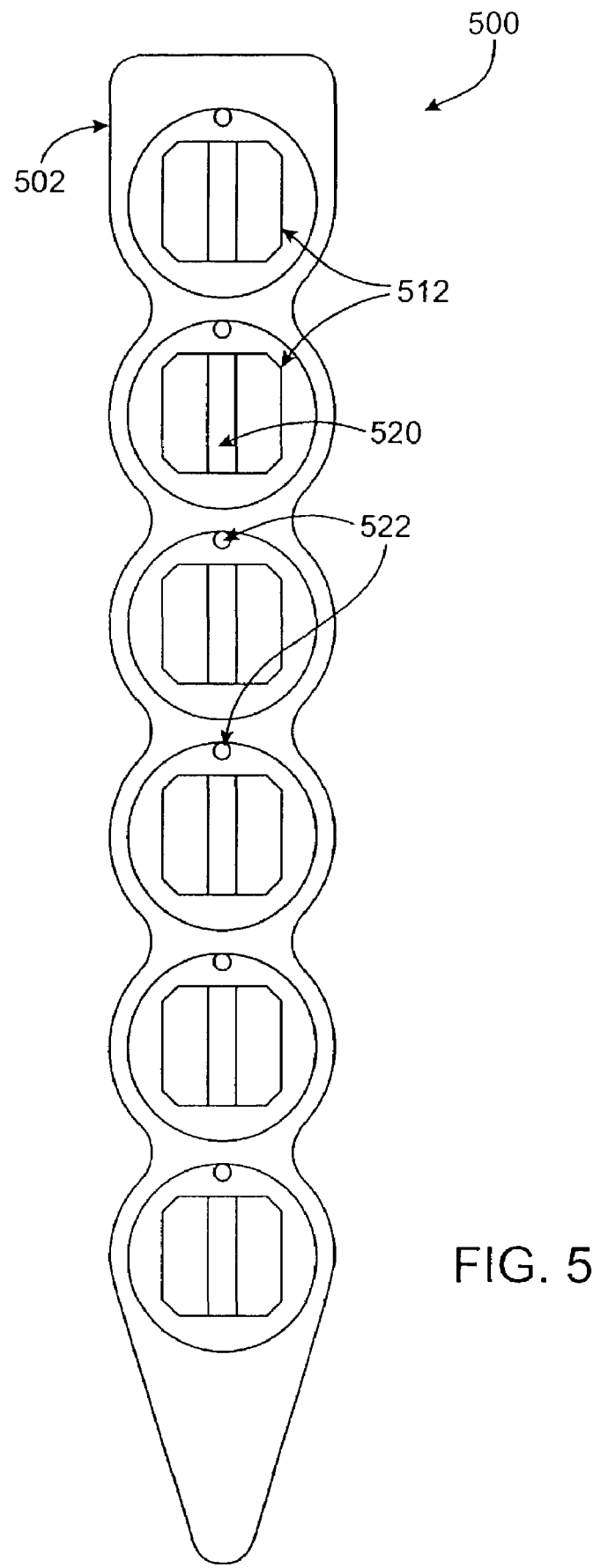
FIG. 5 is a bottom-side view of a flexible, elongate ablation device with one row of suction apertures, according to one embodiment of the invention.

FIG. 5 shows yet another embodiment of ablation device 500, including a tissue contacting member without an ablation member being shown. Device 500 is similar to ablation device 400, but tissue contacting member 502 has one row of suction apertures 512 rather than two and ablation member, placed in ablation trough 520, overlays suction apertures 512. Suction holes 522 shown in suction apertures 512 demonstrate that the apertures sometimes include both a depressed or concave surface and one or more holes communicating with a suction lumen. The embodiment of ablation device 500 in FIG. 5 may be advantageous for forming one or more linear ablations on heart 140 when there is minimal space in which to manipulate device 500 and/or when a narrow, minimally invasive incision or sheath is desired for insertion of device 500. Device 500 may be manufactured from any suitable material or combination of materials, such as those described above, may use any suitable form of ablation member and may include various additional features as desired.

Figure 6:
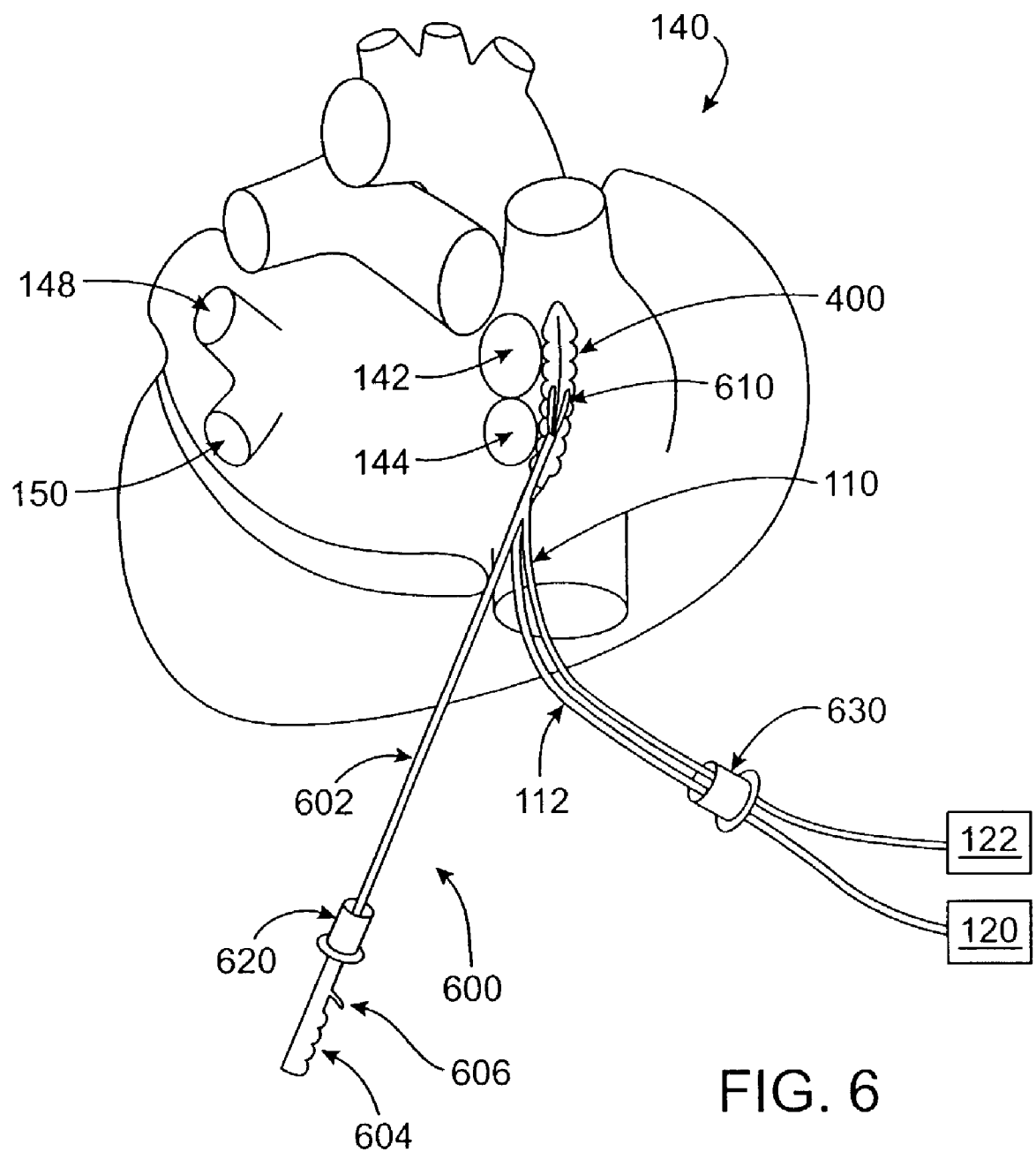
FIG. 6 is a perspective view of a human heart and an ablation device in position for performing an ablation procedure, according to one embodiment of the invention.

Referring now to FIG. 6, ablation device as described with reference to FIGS. 4 and 4a is shown in position for performing epicardial ablation on a human heart 140. Generally, ablation device 400 may be placed in any desired position on heart 140 for ablating epicardial tissue. Thus, in various embodiments device may be placed adjacent one or both of the right pulmonary veins 142, 144, adjacent one or both of the left pulmonary veins 148, 150, or in any other suitable location. Furthermore, ablation device 400 may be used to ablate tissue in a linear pattern at one location and then may be moved to ablated tissue in a linear pattern in another location. As discussed above with reference to various embodiments, ablation device 400 may be introduced into a patient via a minimally invasive device, such as a sheath 630 or trocar, and may be coupled with a source of suction 120 via a suction cannula 112 and with a source of ablative energy 122 via a wire 110 or other connective device.

Ablative device 400, as well as other embodiments of ablative devices described above, may be positioned on heart 140 via a positioning device 602 which is introduced via a second minimally invasive incision or second sheath 620. Second sheath 620 may be placed at any suitable location on the patient to allow access to ablation device with the positioning device 602. Positioning device 602 may then be introduced through sheath and advanced to the position of ablation device 400. Positioning device 602 may then be used to secure device 400, such as by opposable jaws 610 or any other suitable means, and position device 400 in a desired location on heart 140. In some embodiments, positioning device may further be used to reposition device 400 to perform ablation in multiple locations on heart 140.

The proximal end of positioning device 602 may include a handle 604 for holding and manipulating device 602 and one or more actuators 606, such as a trigger for opening and closing opposable jaws 610 or other distally positioned end effectors of device 602. Examples of positioning device 602 may include, but are not limited to, conventional minimally invasive surgical devices such as laproscopic surgical devices and the like.

Referring now to FIG. 7, another embodiment of ablation device 700 suitably includes at least one elongate shaft 702 having a proximal end 724 and a distal end 726, a jaw member 704 coupled with shaft 702 near distal end 726, at least one ablation member 712, 714 coupled with jaw member 704, and a handle 706 and at least one actuator 708, 710 near the proximal end 724 for manipulating device 700, opening and closing the jaw member, activating ablation member 712, 714 and the like. Device 700 is generally configured to be introduced through a minimally invasive sheath, trocar or incision, though it may also be used in open surgical procedures. Shaft 702 may be made of any suitable material, such as metal, ceramic, polymers or any combination thereof, and may be rigid along its entire length or rigid in parts and flexible in one or more parts. In various embodiments, the shaft may be malleable, may articulate about at least one joint and/or may be steerable for positioning the device. In some embodiments, the ablation member is coupled with a portion of the shaft.

Jaw member 704 may be disposed on or near distal end 726 of shaft 702 and is generally configured to open and close to grasp epicardial or other tissue between the opposing jaws. For example, jaw member 704 may be coupled with shaft 702 at a hinge point 730 to allow for such opening and closing motion. An ablation member is coupled with at least part of jaw member 704. As with the above-described embodiments, the ablation member may use any suitable energy source for ablating tissue. In some embodiments, multiple ablation members 712, 714 may be used. For example, one electrode 712 of a bipolar ablation member may be coupled with one opposing jaw and another electrode 714 may be coupled with the other opposing jaw. Alternatively, ablation members 712, 714 may include one unipolar ablation device or any of the ablation devices described with reference to various embodiments above. The jaw member and/or the ablation member may be shaped to contact and ablate the epicardial tissue in a pattern such as, but not limited to, a U-shaped pattern, an L-shaped pattern, a circular pattern or a linear pattern. Actuators 708, 710 may have one or more various functions, such as opening and closing jaw member 704, activating ablation members 712, 714, changing an angle of orientation of jaw member 704, straightening or bending jaw member 704 and/or the like. One actuator 710, for example, may comprise a trigger-like actuator while another actuator 708 may comprise a turnable dial.

Generally, jaw member 704 may have any suitable configuration for contacting a surface of a heart, for grasping epicardial or other tissue to be ablated and/or for placing ablation members 712, 714 in contact with tissue to be ablated. As such, jaw members 714 may be straight, curved, bent or otherwise configured for contacting, grasping and/or ablating tissue. In some embodiments, jaw member 704 may be adjustable via an actuator 708, 710, so as to allow their shapes to be bent, straightened or the like during a procedure. With reference to FIG. 7a, one embodiment of a straight jaw member 718 may allow jaw member 718 to be retracted within shaft (arrows). Retraction may help protect a patient as well as jaw member during insertion and advancement of the device within the patient. Again, ablation members 720, 722 on such straight jaw members 718 may be bipolar RF members, unipolar RF members or any other suitable ablation devices.

Optionally, the device may further include an insulation member at least partially surrounding the device to protect body structures in the vicinity of the epicardial tissue to be ablated from damage due to heat or electrical current. Also optionally, the ablation member may be adjustable to deliver two or more varying amounts of ablative energy to two or more locations on the epicardial tissue. Various embodiments may further include at least one sensor for sensing a quantity of ablation provided by the ablation member to the tissue.

Figure 8:
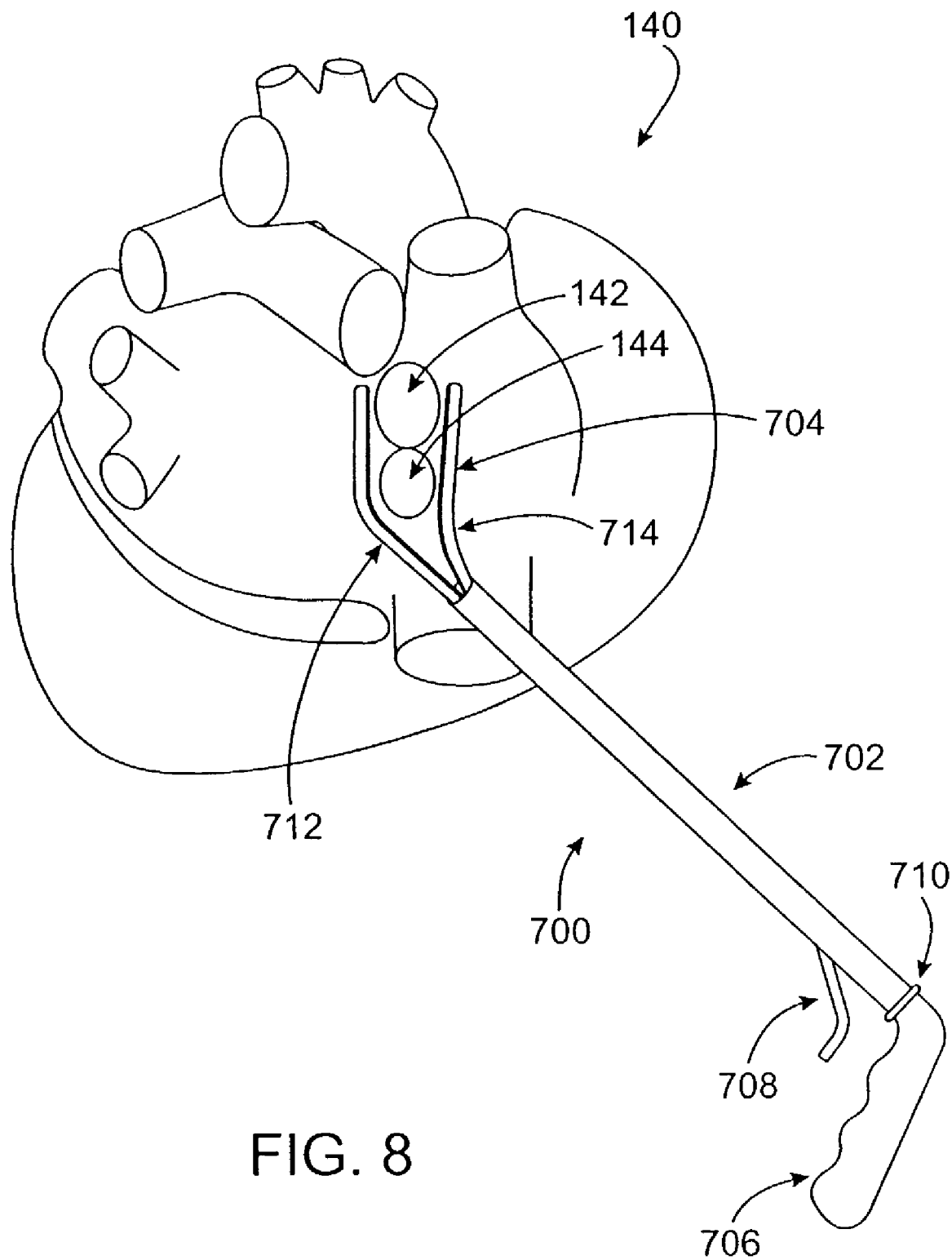
FIG. 8 is a perspective view of a human heart and an elongate shaft ablation device in position for ablating cardiac tissue, according to one embodiment of the invention.

FIG. 8 shows ablation device 700, as just described, in a position for performing an ablation procedure on epicardial tissue of heart 140. Device as shown will ablate in a pattern approximating two lines adjacent the right pulmonary veins 142, 144. It should be understood, from the foregoing descriptions of various embodiments, that jaw member 704 and ablation members 712, 714 could alternatively be configured in any other suitable shape, size or configuration to ablate in other patterns on heart 140. Additionally, device 700 may be moved to a variety of positions to ablate multiple patterns in multiple locations on the epicardial tissue.

Figure 9:
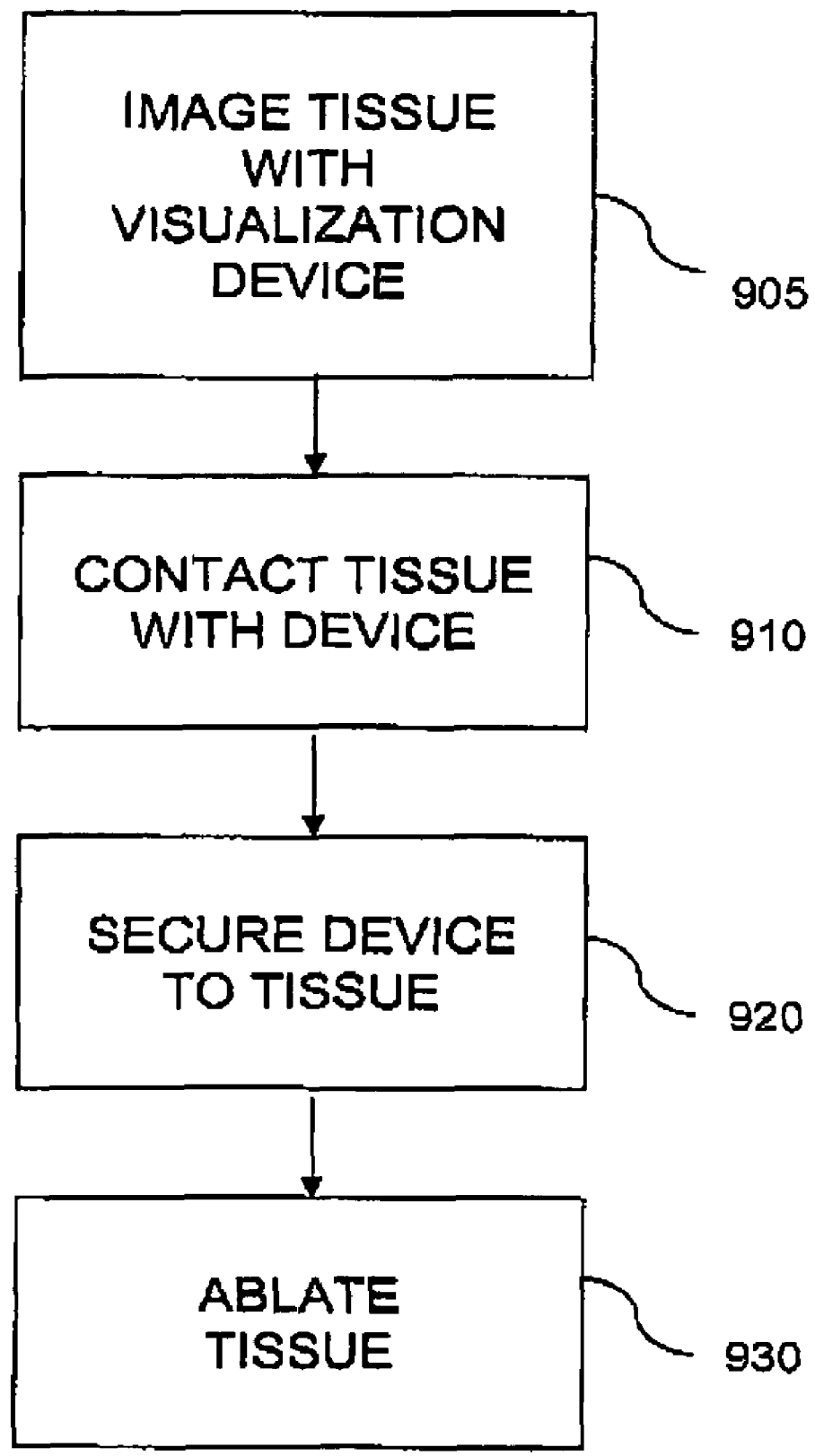
FIG. 9 is a block diagram of a method for ablating tissue according to one embodiment of the invention.

With reference now to FIG. 9, a method for ablating cardiac tissue, such as epicardial tissue, suitably includes contacting cardiac tissue with an ablation device 910, securing the device to the tissue 920 and ablating at least a portion of the contacted, secured tissue 930. Various embodiments of the invention will utilize additional steps or sub-steps of these three basic steps, but it should be emphasized that any additional steps or variations are optional. For example, in some embodiments, contacting the cardiac tissue 910 is preceded by advancing the device into the patient through a minimally invasive introducer device. Contacting the device with the tissue 910 may include positioning the device using a positioning arm or other positioning device. In some embodiments, securing the device to the tissue 920 may also comprise invaginating a portion of epicardial tissue partially within one or more suction apertures and/or may include using one or more suction apertures to dissect through fatty tissue disposed over epicardium. Securing the device 920 may also involve securing with enough force to allow stabilization and/or positioning of the heart itself. And ablation of epicardial tissue 930 may involve ablation in any location or pattern as described above with reference to the inventive devices. Therefore, the descriptions of various methods provided herein are offered for exemplary purposes only and should not be interpreted to limit the scope of the invention as described in the claims.

Other aspects of a method for ablating epicardial tissue may include imaging the epicardial tissue arid an area surrounding the tissue to be ablated, using a visualization device 905. Such a device may be coupled with the ablation device or may be a separate imaging device. In some embodiments, an insufflation device may be inserted between the epicardium and the pericardium and insufflation fluid or gas may be introduced to form a space between the epicardium and pericardium. The space may be used to enhance visualization, allow for freer manipulation of devices near the site for ablation and the like. Another aspect may include sensing ablation of epicardial tissue with one or more sensors, as described above. In some embodiments, tissue may optionally be cooled via a cooling member and/or irrigation of fluid into contact with the tissue. Finally, the actual ablation of epicardial tissue may be accomplished with any suitable ablation member and form of energy, including RF, thermoelectric, cryogenic, microwave, laser, ultrasound or the like. In one embodiment, ablation is achieved and/or enhanced by delivery of one or more drugs to the tissue.

In one embodiment, a method first includes advancing an ablation device through a minimally invasive introducer device into a patient and to a location for ablating epicardial tissue. The device is then contacted with the epicardial tissue and positioned on the tissue with a positioning arm or other device inserted through the same or a separate minimally invasive introducer or incision. Positioning device, in some embodiments, may be a flexible, rigidifying positioner which allows for positioning and then stabilizing with the same device. The ablation device may be placed in any suitable location for ablating epicardial tissue. In one embodiment, for example, ablation device will contact tissue at least partially encircling two pulmonary veins, such as the right superior and right inferior pulmonary veins. The ablation device may contact epicardial tissue directly adjacent the bases of the veins but may be configured to maintain a safe distance between the ablation member on the device and the actual veins.

Once the epicardial tissue is contacted, the device may be secured to the tissue by securing means, such as suction or adhesive. In fact, the device may be secured to the tissue sufficiently in some embodiments to allow the heart to be stabilized and/or positioned using the device and a positioner. For example, a beating heart may be stabilized to reduce or eliminate motion during an ablation procedure or may be pulled, turned or otherwise moved into an advantageous position for ablating, visualizing or treating the heart. Suction force may also be supplied in sufficient strength to dissect through a layer of adipose tissue overlying the epicardial tissue, which may provide improved contact of an ablation member with the epicardial tissue. Once the tissue is secured, at least a portion of the tissue may be ablated by delivering energy to an ablation member (or members) on the device. As already described in detail, such energy may include any suitable energy and may additionally or alternatively include one or more ablative drugs. After ablation, tissue may be cooled via cooling means and/or ablation of tissue may be sensed with one or more sensors. When an ablative procedure is complete, the device may be removed and placed in another location on the heart for an additional procedure or may be removed from the patient altogether.

Figure 10:
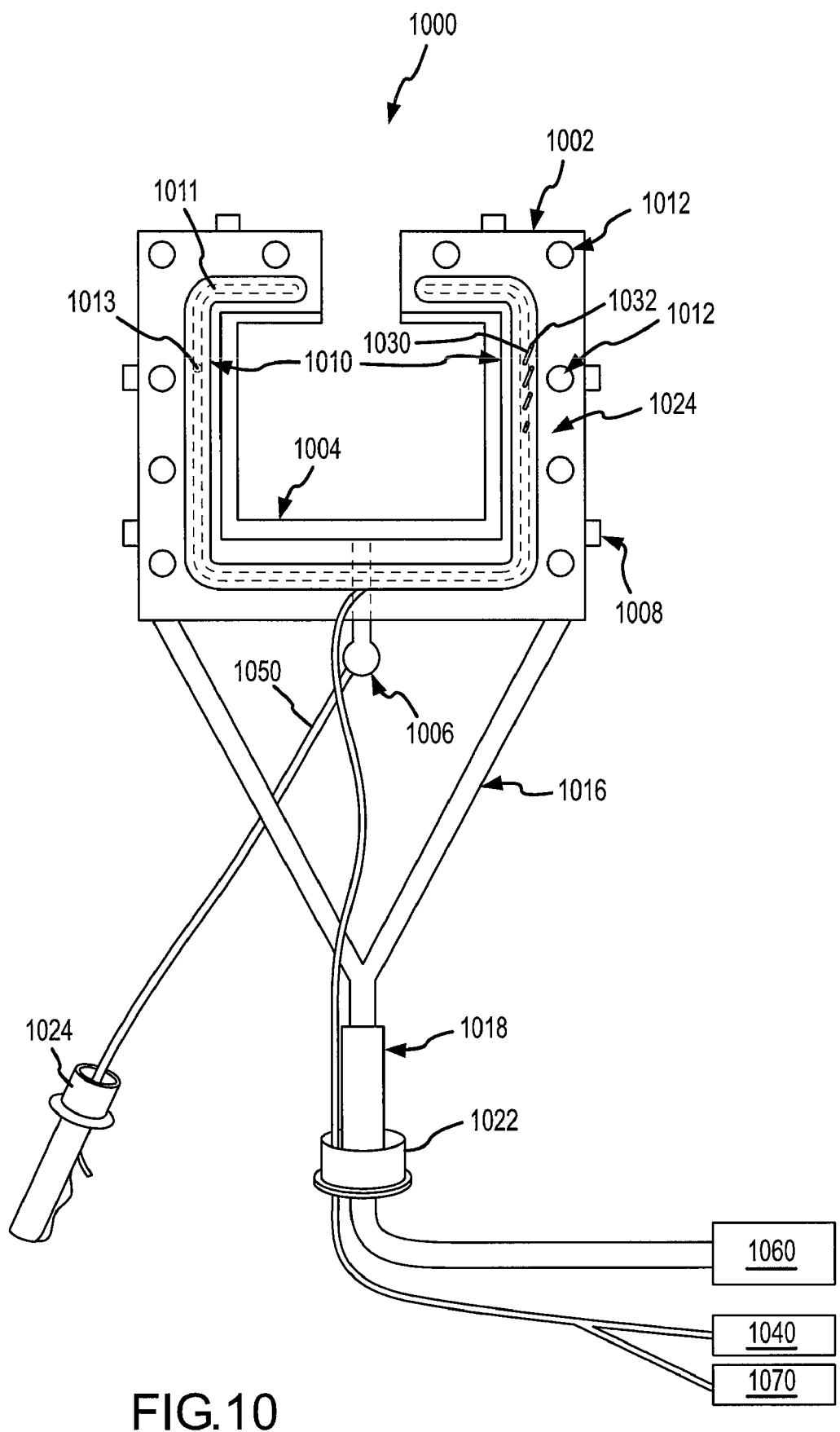
FIG. 10 illustrates a system for treating heart tissue according to embodiments of the present invention

FIG. 10 illustrates a system 1000 for treating heart tissue according to embodiments of the present invention. System 1000 includes at least one therapeutic agent transmission member 1010 for applying at least one therapeutic agent to the heart tissue of a patient. System 1000 also includes at least one tissue securing member 1002 coupled with the at least one therapeutic agent transmission member 1010 for enhancing contact of the therapeutic agent transmission member with the heart tissue. System 1000 further includes at least one guiding member 1004 coupled with at least one of the therapeutic agent transmission member 1010 and the tissue securing member 1002 for guiding the therapeutic agent transmission member 1010 and the tissue securing member 1002 to a location for treating the heart tissue. In some embodiments, for example, the therapeutic agent transmission member 1010 includes at least one lumen 1011 and at least one aperture 1013 in the lumen for allowing passage of the at least one therapeutic agent out of the lumen to contact the heart tissue.

System 1000 can also include at least one needle coupled with the therapeutic agent transmission member 1010 for insertion into the heart tissue to enhance application of the at least one therapeutic agent to the heart tissue. For example, the therapeutic agent transmission member 1010 itself may comprise at least one needle 1030 and at least one aperture 1032 adjacent a tip of each needle for allowing passage of the at least one therapeutic agent out of the needle to contact the heart tissue. Optionally, the needle may be retractable. For example, the retractable needle may be exposed and retracted via a pneumatic member 1070 coupled with the therapeutic agent transmission member 1010. In some embodiments, the retractable needle is exposed and retracted automatically when the therapeutic agent transmission member contacts the heart tissue. In some embodiments, a depth of penetration of the retractable needle into the heart tissue is adjustable.

In some embodiments, tissue contacting or securing member 1002 includes a tissue contacting surface 1024, multiple suction apertures 1012, and multiple artery securing arms 1008. Tissue contacting member 1002 can be coupled with a suction cannula 1018 via a V-shaped suction connector 1016. Therapeutic agent transmission member 1010 can be coupled with, for example, an energy source 1040. Guiding or support member 1004 can include a guiding or support arm 1006 that couples with a positioning device 1050. System 1000 may include a sheath 1022 and a source of suction 1060. As shown here, sheath 1022 can receive the therapeutic agent transmission member 1010, the tissue securing member 1002, or both, through an incision. System 1000 may also include a sheath 1024 for receiving the guiding member or positioning device 1050 through a separate incision. In some embodiments, system 1000 can be positioned on a heart via positioning device 1050 which is introduced via a minimally invasive incision or sheath 1024.

While the present invention has bee shown and described with reference to various embodiment thereof, the above and other changes in form and detail may be made without departing from the spirit and scope of the invention as defined in the following claims.

What is claimed is:

1. A system for treating heart tissue to treat a cardiac arrhythmia, the system comprising:
   at least one energy transmission member for applying energy to the heart tissue in a pattern to treat the cardiac arrhythmia;
   at least one tissue securing member coupled with the at least one energy transmission member for enhancing contact of the energy transmission member with the heart tissue;
   at least one guiding member coupled with at least one of the energy transmission member or the tissue securing member for guiding the energy transmission member and the tissue securing member to a location for treating the heart tissue;
   a connector for removably coupling the at least one tissue securing member with the at least one energy transmission member; and
   at least one positioning device for contacting the heart tissue and positioning the heart tissue for treatment, the at least one positioning device comprising a suction positioning device;
   wherein the at least one tissue securing member is conformable to a surface topography of the heart tissue.

2. A system as in claim 1, further comprising at least one visualization member for enhancing visualization of the heart tissue and the treatment location.

3. A system as in claim 2, wherein the at least one visualization member comprises at least one of an optic imaging device, a thermal imaging device, an ultrasound device, an electrical imaging device or a Doppler imaging device.

4. A system as in claim 3, wherein the optic imaging device comprises a fiber optic device positionable to view a posterior portion of the heart tissue.

5. A system as in claim 3, wherein the thermal imaging device measures at least one heat transfer coefficient of the heart tissue to determine at least one of a type or a thickness of the heart tissue.

6. A system as in claim 3, wherein the electrical imaging device measures at least one of electrical resistance or impedance of the heart tissue to determine at least one of a type and a thickness of the heart tissue.

7. A system as in claim 2, wherein the at least one visualization member is removably coupled with at least one of the at least one energy transmission member, the at least one tissue securing member or the at least one guiding member.

8. A system as in claim 2, wherein the at least one visualization member comprises at least one optic member for acquiring optic signals of an area to be visualized, and wherein the visualization member includes at least one inflatable member coupled with the visualization member at or near the optic member.

9. A system as in claim 8, wherein the at least one inflatable member provides a space in a body cavity to enhance operation of the optic member.

10. A system as in claim 8, wherein the at least one inflatable member provides a space between at least two body tissues to enhance operation of the optic member.

11. A system as in claim 8, wherein the at least one inflatable member comprises an inflation port in fluid communication with an inflation lumen coupled with the visualization member for allowing introduction of a liquid or a gas to inflate the inflatable member.

12. A system as in claim 8, wherein the at least one inflatable member reduces motion of the heart tissue when applied to the heart tissue.

13. A system as in claim 1, wherein the at least one positioning device reduces motion of a beating heart to further position the heart tissue for treatment.

14. A system as in claim 1, wherein the at least one energy transmission member contacts an epicardial surface of the heart tissue to transmit the energy, and wherein the energy is transmitted from the epicardial surface through the heart tissue to an endocardial surface.

15. A system as in claim 14, wherein the energy is further transmitted through at least one of fat and connective tissue covering at least part of the epicardial surface.

16. A system as in claim 1, wherein at least one energy transmission member is coupled with at least one guiding member such that a change in shape of the guiding member causes a corresponding change in shape of the energy transmission member.

17. A system as in claim 16, wherein the guiding member comprises a deformable linear member its shape being adjustable by a user, and wherein the energy transmission member comprises a deformable linear member coaxially coupled with the guiding member so as to move with the guiding member.

18. A system as in claim 17, wherein the guiding member is adjustable to at least partially encircle at least one pulmonary vein.

19. A system as in claim 1, wherein a first longitudinal axis of the tissue securing member and a second longitudinal axis of the removably coupled energy transmission member are parallel to one another.

20. A system as in claim 1, wherein a first longitudinal axis of the tissue securing member and a second longitudinal axis of the removably coupled energy transmission member are offset from one another.

21. A system as in claim 1, wherein the at least one energy transmission member comprises a linear member, and wherein the at least one connector comprises a plurality of connectors disposed along a length of the tissue securing member for removably coupling the linear member with the tissue securing member.

22. A system as in claim 1, wherein the at least one tissue securing member allows compressive force to be applied between the at least one energy transmission member and the heart tissue.

23. A system as in claim 1, wherein the at least one tissue securing member comprises at least one expansible balloon member.

24. A system as in claim 23, wherein the at least one expansible balloon member comprises at least one fluid introduction port for allowing introduction of a liquid or a gas to expand the balloon member.

25. A system as in claim 24, wherein the at least one expansible balloon member comprises multiple, separate balloon members, and wherein each separate balloon member is in fluid communication with a separate fluid introduction port.

26. A system as in claim 25, further comprising means for selectively introducing fluid into one or more of the separate balloons without introducing fluid into one or more other separate balloons.

27. A system as in claim 1, wherein the tissue securing member prevents a portion of the heart tissue from being treated by the at least one energy transmission member.

28. A system as in claim 27, wherein the tissue securing member comprises at least one insulation material for preventing the portion of the heart tissue from being treated.

29. A system as in claim 28, wherein the at least one insulation material further prevents the at least one energy transmission member from contacting or harming other, non-cardiac tissue of the patient and from contacting or harming a user of the energy transmission member.

30. A system as in claim 1, wherein the at least one guiding member comprises at least one of an elongate shaft, a steerable guidewire and an introducer sheath.

31. A system as in claim 30, wherein the steerable guidewire comprises a pushable guidewire having at least one relatively stiff portion and one relatively flexible portion for positioning the energy transmission member in a location for treatment.

32. A system as in claim 30, wherein the steerable guidewire comprises a pullable guidewire to which tension is applied to steer the guidewire to position the energy transmission member in a location for treatment.

33. A system for treating heart tissue to treat a cardiac arrhythmia, the system comprising:
at least one energy transmission member for applying energy to the heart tissue in a pattern to treat the cardiac arrhythmia;
at least one tissue securing member coupled with the at least one energy transmission member for enhancing contact of the energy transmission member with the heart tissue;
at least one needle coupled with the energy transmission member for insertion into the heart tissue to enhance the application of energy to the heart tissue;
at least one guiding member coupled with at least one of the energy transmission member or the tissue securing member for guiding the energy transmission member and the tissue securing member to a location for treating the heart tissue; and
a connector for removably coupling the at least one tissue securing member with the at least one energy transmission member;
wherein the applied energy is selected from the group consisting of radio frequency energy, ultrasound energy, microwave energy, cryogenic energy, thermoelectric energy and laser energy.

34. A system as in claim 33, further comprising at least one grounding device for dispersing the energy from a patient undergoing an energy transmission heart procedure.

35. A system as in claim 33, wherein the energy is transmitted from a tip of each of the at least one needle.

36. A system as in claim 33, wherein the at least one needle is retractable.

37. A system as in claim 36, wherein the at least one retractable needle is exposed and retracted via a pneumatic member coupled with the energy transmission member.

38. A system as in claim 36, wherein the at least one retractable needle is exposed and retracted automatically when the energy transmission member contacts the heart tissue.

39. A system as in claim 36, wherein a depth of penetration of the at least one retractable needle into the heart tissue is adjustable.

40. A system as in claim 33, further comprising at least one closed circuit feedback loop for measuring and regulating operation of the energy transmission member.

41. A system as in claim 33, wherein at least one of the energy transmission member or the tissue securing member further comprises at least one fluid aperture for applying fluid to the heart tissue to enhance the application of energy to the heart tissue.

42. A system for treating heart tissue to treat a cardiac arrhythmia, the system comprising:
at least one energy transmission member for applying energy to the heart tissue in a pattern to treat the cardiac arrhythmia;
at least one tissue securing member coupled with the at least one energy transmission member for enhancing contact of the energy transmission member with the heart tissue;
at least one guiding member coupled with at least one of the energy transmission member or the tissue securing member for guiding the energy transmission member and the tissue securing member to a location for treating the heart tissue; and
a connector for removably coupling the at least one tissue securing member with the at least one energy transmission member;
wherein a first longitudinal axis of the tissue securing member and a second longitudinal axis of the removably coupled energy transmission member are colinear.

43. A system for treating heart tissue to treat a cardiac arrhythmia, the system comprising:
at least one energy transmission member for applying energy to the heart tissue in a pattern to treat the cardiac arrhythmia;

at least one tissue securing member coupled with the at least one energy transmission member for enhancing contact of the energy transmission member with the heart tissue;

at least one guiding member coupled with at least one of the energy transmission member or the tissue securing member for guiding the energy transmission member and the tissue securing member to a location for treating the heart tissue; and a connector for removably coupling the at least one tissue securing member with the at least one energy transmission member;

wherein the at least one tissue securing member comprises at least one vacuum applying member.

44. A system as in claim 43, wherein the at least one vacuum applying member comprises:
at least one vacuum lumen;
at least one vacuum port in fluid communication with the lumen for coupling the lumen with a vacuum source; and
at least one aperture in fluid communication with the lumen for applying vacuum force to the heart tissue.

45. A system as in claim 44, wherein the at least one vacuum lumen comprises multiple, separate lumens, and wherein each separate lumen is in fluid communication with a separate vacuum port.

46. A system as in claim 45, further comprising means for selectively applying vacuum to one or more of the separate lumens without applying vacuum to one or more other separate lumens.

47. A system for treating heart tissue to treat a cardiac arrhythmia, the system comprising:
at least one therapeutic agent transmission member for applying at least one therapeutic agent to the heart tissue in a pattern to treat the cardiac arrhythmia;
at least one tissue securing member coupled with the at least one therapeutic agent transmission member for enhancing contact of the at least one therapeutic agent transmission member with the heart tissue;
at least one guiding member coupled with at least one of the therapeutic agent transmission member or the tissue securing member for guiding the therapeutic agent transmission member and the tissue securing member to a location for treating the heart tissue;
a first sheath for receiving the at least one guiding member through a first incision; and
a second sheath for receiving at least one of the therapeutic agent transmission member or the tissue securing member through a second incision.

48. A system as in claim 47, wherein the therapeutic agent transmission member comprises:
at least one lumen; and
at least one aperture in the lumen for allowing passage of the at least one therapeutic agent out of the lumen to contact the heart tissue.

49. A system as in claim 48, further comprising at least one needle coupled with the therapeutic agent transmission member for insertion into the heart tissue to enhance application of the at least one therapeutic agent to the heart tissue.

50. A system as in claim 47, wherein the therapeutic agent transmission member comprises:
at least one needle; and
at least one aperture adjacent a tip of each needle for allowing passage of the at least one therapeutic agent out of the needle to contact the heart tissue.

51. A system as in claim 50, wherein the at least one needle is retractable.

52. A system as in claim 51, wherein the at least one retractable needle is exposed and retracted via a pneumatic member coupled with the therapeutic agent transmission member.

53. A system as in claim 51, wherein the at least one retractable needle is exposed and retracted automatically when the therapeutic agent transmission member contacts the heart tissue.

54. A system as in claim 51, wherein a depth of penetration of the at least one retractable needle into the heart tissue is adjustable.

55. A method for treating heart tissue of a patient to treat a cardiac arrhythmia, the method comprising:
advancing at least one treatment member coupled with at least one tissue securing member through a first incision on the patient;
inserting at least one guiding member through a second incision on the patient and securing the at least one guiding member with at least one of the treatment member and the tissue securing member;
visualizing a treatment area in the patient with at least one visualization member;
contacting the heart tissue of the patient with the at least one treatment member and the at least one tissue securing member by manipulating the at least one guiding member;
applying a force, through at least one of the tissue securing member or the guiding member, to enhance contact of the at least one treatment member with the heart tissue; and
treating the heart tissue, using the at least one treatment member.

56. A method as in claim 55, wherein at least one of the treatment member or the tissue securing member are advanced through a port applied to the patient, the port having a diameter no greater than 5 cm.

57. A method as in claim 55, wherein the advancing step includes guiding at least one of the treatment member or the tissue securing member using at least one guiding member.

58. A method as in claim 57, wherein guiding comprises using a pushable guidewire having at least one relatively stiff portion and one relatively flexible portion for positioning the treatment member in a location for treatment.

59. A method as in claim 57, wherein guiding comprises using a pullable guidewire to which tension is applied to steer the guidewire to position the treatment member in a location for treatment.

60. A method as in claim 55, further comprising using at least one positioning device to position the heart tissue for treatment.

61. A method as in claim 60, wherein using the at least one positioning device comprises applying suction to the heart tissue.

62. A method as in claim 60, wherein using the at least one positioning device reduces motion of the heart tissue.

63. A method as in claim 55, wherein contacting the heart tissue comprises applying a suction force with the tissue securing member to increase a contact surface area of the tissue securing member with the heart tissue.

64. A method as in claim 63, wherein applying the suction force further comprises providing consistent contact force between the heart tissue and the tissue securing member.

65. A method as in claim 63, wherein applying the suction force comprises securing the tissue securing member and the treatment member to the heart tissue, the tissue securing member and the treatment member having the same cross-sectional shape.

66. A method as in claim 55, wherein treating the heart tissue comprises applying energy to the heart tissue in a pattern to reduce or eliminate the cardiac arrhythmia.

67. A method as in claim 66, wherein applying the energy comprises applying at least one of radio frequency energy, ultrasound energy, microwave energy, cryogenic energy, thermoelectric energy or laser energy.

68. A method as in claim 66, wherein applying the energy comprises applying energy to an epicardial surface of the heart, and wherein the energy is transmitted from the epicardial surface through the heart tissue to an endocardial surface.

69. A method as in claim 68, wherein the energy is further transmitted through at least one of fat and connective tissue covering at least part of the epicardial surface.

70. A method as in claim 66, further comprising dispersing the energy from the patient through at least one grounding device coupled with the patient.

71. A method as in claim 66, further comprising inserting at least one needle into the heart tissue to enhance the application of energy to the heart tissue.

72. A method as in claim 71, wherein the energy is transmitted from a tip of each of the at least one needle.

73. A method as in claim 71, further comprising extending the at least one needle from a retracted position before applying the energy and retracting the at least one needle to the retracted position when the energy has been applied.

74. A method as in claim 73, further comprising selecting a depth of penetration of the at least one retractable needle into the heart tissue.

75. A method as in claim 66, further comprising:
measuring the application of energy to the heart tissue using at least one closed circuit feedback loop; and
regulating the application of energy to the heart tissue based on the measurement.

76. A method as in claim 66, further comprising applying fluid to the heart tissue to enhance the application of energy to the heart tissue.

77. A method as in claim 55, wherein treating the heart tissue comprises applying at least one therapeutic agent to the heart tissue in a pattern to reduce or eliminate the cardiac arrhythmia.

78. A method as in claim 77, wherein applying the at least one therapeutic agent comprises infusing the agent through at least one aperture in the at least one treatment member.

79. A method as in claim 78, applying the at least one therapeutic agent comprises infusing the agent through at least one aperture in at least one needle coupled with the treatment member.

80. A method as in claim 77, wherein applying the at least one therapeutic agent comprises:
inserting at least one needle into the heart tissue to a desired depth;
injecting the at least one agent into the heart tissue; and
removing the at least one needle from the heart tissue.

81. A method as in claim 80, further comprising:
extending the at least one needle from a retracted position for insertion into the heart tissue; and
retracting the at least one needle to the retracted position after injection.

82. A method as in claim 55, further including adjusting a shape of a guiding member coupled with the at least one treatment member to alter the shape of the treatment member.

83. A method as in claim 82, wherein adjusting the shape of the guiding member allows the treatment member to conform to a surface of the heart tissue.

84. A method as in claim 82, wherein adjusting the shape of the guiding member allows the treatment member to at least partially encircle at least one pulmonary vein.

85. A method as in claim 55, further comprising removably coupling the tissue securing member with the at least one treatment member.

86. A method as in claim 85, further comprising conforming the tissue securing member to a surface topography of the heart tissue.

87. A method as in claim 55, wherein applying force comprises applying compressive force between the at least one treatment member and the heart tissue.

88. A method as in claim 87, wherein applying the compressive force comprises applying vacuum force via at least one vacuum member of the tissue securing member.

89. A method as in claim 88, further comprising applying the vacuum force through at least a portion of the vacuum member while not applying the vacuum force through at least another portion of the vacuum member.

90. A method as in claim 87, wherein applying the compressive force comprises applying force via at least one expansible balloon member.

91. A method as in claim 87, further comprising preventing, using the tissue securing member, a portion of the heart tissue from being treated by the at least one treatment member.

92. A method as in claim 91, wherein the tissue securing member comprises at least one insulation material for preventing the portion of the heart tissue from being treated.

93. A method as in claim 55, visualizing comprises using at least one visualization member selected from the group consisting of an optic imaging device, a thermal imaging device, an ultrasound device, an electrical imaging device and a Doppler imaging device.

94. A method as in claim 93, further comprising expanding an expansible balloon coupled with the visualization member near an optic element to enhance visualization.

95. A method as in claim 94, wherein expanding the balloon provides a space in a body cavity to enhance operation of the optic member.

96. A method as in claim 94, wherein expanding the balloon provides a space between at least two body tissues to enhance operation of the optic member.

97. A method as in claim 94, wherein expanding the balloon reduces motion of the heart tissue when applied to the heart tissue.

98. A method for treating heart tissue of a patient to treat a cardiac arrhythmia, the method comprising:
advancing at least one treatment member and at least one tissue securing member through an incision on the patient;
removably coupling the at least one treatment member with the at least one tissue securing member;
visualizing a treatment area in the patient with at least one visualization member;
contacting the heart tissue of the patient with the treatment member and the tissue securing member;
applying a force, through the tissue securing member, to enhance contact of the treatment member with the heart tissue; and
treating the heart tissue, using the at least one treatment member.

99. A method as in claim 98, wherein the treatment member is advanced through the tissue securing member.

100. A method as in claim 98, wherein the treatment member and the tissue securing member are advanced through a minimally invasive port applied to the patient.

101. A method as in claim 55, wherein the at least one treatment member and the at least one tissue securing member are advanced through the first incision via a first sheath applied to the patient, and wherein the at least one guiding member is advanced through the second incision via a second sheath applied to the patient.

* * * * *